United States Patent
Weitzner et al.

(10) Patent No.: US 11,832,789 B2
(45) Date of Patent: Dec. 5, 2023

(54) DEVICES, SYSTEMS, AND METHODS FOR MINIMALLY INVASIVE SURGERY IN A BODY LUMEN

(71) Applicant: Boston Scientific Scimed, Inc., Maple Grove, MN (US)

(72) Inventors: Barry Weitzner, Acton, MA (US); George T. Roberts, Lincoln, MA (US); Paul Smith, Smithfield, RI (US); Gregory Piskun, Delray Beach, FL (US); John T. To, Newark, CA (US); Jeffrey P. Radziunas, Wallingford, CT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 182 days.

(21) Appl. No.: 17/114,809

(22) Filed: Dec. 8, 2020

(65) Prior Publication Data

US 2021/0177244 A1    Jun. 17, 2021

Related U.S. Application Data

(60) Provisional application No. 62/947,659, filed on Dec. 13, 2019.

(51) Int. Cl.
*A61B 1/00* (2006.01)
*A61B 1/018* (2006.01)
*A61B 17/00* (2006.01)

(52) U.S. Cl.
CPC ...... *A61B 1/00085* (2013.01); *A61B 1/00066* (2013.01); *A61B 1/00133* (2013.01);
(Continued)

(58) Field of Classification Search
CPC ............ A61B 1/00066; A61B 1/00085; A61B 1/00133; A61B 1/018; A61B 1/005;
(Continued)

(56) References Cited

U.S. PATENT DOCUMENTS

| 457,787 A | 8/1891 | Leisenring |
| 1,621,159 A | 3/1927 | Evans |

(Continued)

FOREIGN PATENT DOCUMENTS

| CN | 1579352 A | 2/2005 |
| CN | 101048101 A | 10/2007 |

(Continued)

OTHER PUBLICATIONS

European Communication for European Patent Application No. 14733912.1, dated Jun. 11, 2018, 2 pages.
(Continued)

*Primary Examiner* — Ryan N Henderson
(74) *Attorney, Agent, or Firm* — Seager, Tufte & Wickhem, LLP

(57) ABSTRACT

Improved methods and devices for performing an endoscopic surgery are provided. Systems are taught for operatively treating gastrointestinal disorders endoscopically in a stable, yet dynamic operative environment, and in a minimally invasive manner. Such systems include, for example, an endoscopic surgical suite. The surgical suite can have a reversibly expandable retractor that expands to provide a stable, operative environment within a subject. The expansion can be selectively asymmetric to maximize space for a tool and an endoscope to visualize a target tissue and treat the target tissue from outside the patient in a minimally invasive manner.

14 Claims, 25 Drawing Sheets

(52) U.S. Cl.
CPC ...... *A61B 1/00135* (2013.01); *A61B 1/00137* (2013.01); *A61B 1/018* (2013.01); *A61B 17/00234* (2013.01); *A61B 2017/0034* (2013.01); *A61B 2017/00353* (2013.01)

(58) Field of Classification Search
CPC ...... A61B 17/00234; A61B 2017/0034; A61B 2017/00353
See application file for complete search history.

(56) References Cited

U.S. PATENT DOCUMENTS

| | | |
|---|---|---|
| 2,434,167 A | 1/1948 | Knoblauch |
| 3,517,128 A | 6/1970 | Hines |
| 4,040,413 A | 8/1977 | Ohshiro |
| 4,083,369 A | 4/1978 | Sinnreich |
| 4,224,929 A | 9/1980 | Furihata |
| 4,295,464 A | 10/1981 | Shihata |
| 4,519,403 A | 5/1985 | Dickhudt |
| 4,611,594 A | 9/1986 | Grayhack et al. |
| 4,710,171 A | 12/1987 | Rosenberg |
| 4,718,406 A | 1/1988 | Bregman et al. |
| 4,836,204 A | 6/1989 | Landymore et al. |
| 4,966,596 A | 10/1990 | Kuntz et al. |
| 5,025,778 A | 6/1991 | Silverstein et al. |
| 5,059,199 A | 10/1991 | Okada et al. |
| 5,087,265 A | 2/1992 | Summers |
| 5,112,310 A | 5/1992 | Grobe |
| 5,167,239 A | 12/1992 | Cohen et al. |
| 5,197,971 A | 3/1993 | Bonutti |
| 5,211,624 A | 5/1993 | Cinberg et al. |
| 5,211,638 A | 5/1993 | Dudar et al. |
| 5,386,817 A | 2/1995 | Jones |
| 5,411,475 A | 5/1995 | Atala et al. |
| 5,411,508 A | 5/1995 | Bessler et al. |
| 5,423,830 A | 6/1995 | Schneebaum et al. |
| 5,454,365 A | 10/1995 | Bonutti |
| 5,655,698 A | 8/1997 | Yoon |
| 5,709,657 A | 1/1998 | Zimmon |
| 5,716,321 A | 2/1998 | Kerin et al. |
| 5,722,103 A | 3/1998 | Walega |
| 5,776,097 A | 7/1998 | Massoud |
| 5,947,983 A | 9/1999 | Solar et al. |
| 5,954,731 A | 9/1999 | Yoon |
| 5,997,547 A | 12/1999 | Nakao et al. |
| 6,009,877 A | 1/2000 | Edwards |
| 6,042,596 A | 3/2000 | Bonutti |
| 6,119,913 A | 9/2000 | Adams et al. |
| 6,142,931 A | 11/2000 | Kaji |
| 6,142,933 A | 11/2000 | Longo et al. |
| 6,203,552 B1 | 3/2001 | Bagley et al. |
| 6,214,024 B1 | 4/2001 | Houser |
| 6,264,086 B1 | 7/2001 | McGuckin, Jr. |
| 6,302,311 B1 | 10/2001 | Adams et al. |
| 6,343,731 B1 | 2/2002 | Adams et al. |
| 6,405,732 B1 | 6/2002 | Edwards et al. |
| 6,423,058 B1 | 7/2002 | Edwards et al. |
| 6,428,473 B1 | 8/2002 | Leonard et al. |
| 6,494,881 B1 | 12/2002 | Bales et al. |
| 6,605,078 B2 | 8/2003 | Adams |
| 6,616,603 B1 | 9/2003 | Fontana |
| 6,695,198 B2 | 2/2004 | Adams et al. |
| 6,749,607 B2 * | 6/2004 | Edwards ............ A61B 18/1477 606/41 |
| 6,805,273 B2 | 10/2004 | Bilotti et al. |
| 6,808,491 B2 | 10/2004 | Kortenbach et al. |
| 6,840,423 B2 | 1/2005 | Adams et al. |
| 6,866,178 B2 | 3/2005 | Adams et al. |
| 6,874,669 B2 | 4/2005 | Adams et al. |
| 6,913,610 B2 | 7/2005 | Nakao |
| 6,923,806 B2 | 8/2005 | Hooven et al. |
| 6,938,814 B2 | 9/2005 | Sharma et al. |
| 7,014,646 B2 | 3/2006 | Adams |
| 7,059,331 B2 | 6/2006 | Adams et al. |
| 7,063,659 B2 | 6/2006 | Goto et al. |
| 7,169,115 B2 | 1/2007 | Nobis et al. |
| 7,276,066 B2 | 10/2007 | Ouchi |
| 7,396,329 B2 | 7/2008 | Nakao |
| 7,445,598 B2 | 11/2008 | Orban, III |
| 7,918,787 B2 | 4/2011 | Saadat |
| 7,959,559 B2 | 6/2011 | Yamaya |
| 8,007,508 B2 | 8/2011 | Cox |
| 8,277,373 B2 | 10/2012 | Maahs et al. |
| 8,506,479 B2 | 8/2013 | Piskun et al. |
| 8,517,933 B2 | 8/2013 | Mohr |
| 8,608,652 B2 | 12/2013 | Voegele et al. |
| 8,764,630 B2 | 7/2014 | Yamatani |
| 8,777,961 B2 | 7/2014 | Cabrera et al. |
| 8,932,326 B2 | 1/2015 | Riina et al. |
| 8,979,884 B2 | 3/2015 | Milsom et al. |
| 9,039,601 B2 | 5/2015 | Piskun |
| 9,050,004 B2 | 6/2015 | Diao et al. |
| 9,161,746 B2 | 10/2015 | Piskun et al. |
| 9,168,053 B2 | 10/2015 | Cox |
| 9,259,233 B2 | 2/2016 | Gruber et al. |
| 9,370,379 B2 | 6/2016 | Osman |
| 9,375,224 B2 | 6/2016 | Jansen |
| 9,661,984 B2 | 5/2017 | Piskun |
| 10,588,489 B2 * | 3/2020 | Piskun ............... A61B 1/00154 |
| 10,588,504 B2 * | 3/2020 | Piskun ............... A61B 17/0218 |
| 10,933,222 B2 * | 3/2021 | Weitzner .......... A61B 17/00234 |
| 10,966,701 B2 * | 4/2021 | Piskun ............... A61B 1/00087 |
| 11,071,534 B2 * | 7/2021 | Piskun ............... A61B 17/0218 |
| RE48,850 E * | 12/2021 | Piskun ................ A61B 17/221 |
| 11,241,560 B2 * | 2/2022 | Piskun ............... A61B 1/00082 |
| 11,344,285 B2 * | 5/2022 | Piskun ..................... A61B 1/32 |
| 2001/0004947 A1 | 6/2001 | Lemke et al. |
| 2001/0047169 A1 | 11/2001 | McGuckin, Jr. et al. |
| 2001/0049497 A1 | 12/2001 | Kalloo et al. |
| 2001/0056260 A1 | 12/2001 | Grimes et al. |
| 2002/0123748 A1 * | 9/2002 | Edwards ............ A61B 18/1477 606/41 |
| 2002/0183593 A1 | 12/2002 | Chin et al. |
| 2002/0193660 A1 | 12/2002 | Weber et al. |
| 2003/0023143 A1 | 1/2003 | Abe et al. |
| 2003/0050663 A1 | 3/2003 | Khachin et al. |
| 2003/0074015 A1 | 4/2003 | Nakao |
| 2003/0135230 A1 | 7/2003 | Massey et al. |
| 2003/0225432 A1 | 12/2003 | Baptiste et al. |
| 2003/0225433 A1 | 12/2003 | Nakao |
| 2004/0034278 A1 | 2/2004 | Adams |
| 2004/0082859 A1 | 4/2004 | Schaer |
| 2004/0158263 A1 | 8/2004 | McAlister et al. |
| 2004/0204725 A1 | 10/2004 | Bayer |
| 2004/0210116 A1 | 10/2004 | Nakao |
| 2004/0249367 A1 * | 12/2004 | Saadat ................. A61B 1/2736 600/101 |
| 2005/0177105 A1 | 8/2005 | Shalev |
| 2005/0234297 A1 | 10/2005 | Devierre et al. |
| 2005/0234299 A1 | 10/2005 | Eitenmuller et al. |
| 2005/0240147 A1 | 10/2005 | Makower et al. |
| 2005/0251111 A1 | 11/2005 | Saito et al. |
| 2005/0251177 A1 | 11/2005 | Saadat et al. |
| 2005/0272977 A1 | 12/2005 | Saadat et al. |
| 2005/0273085 A1 | 12/2005 | Hinman et al. |
| 2006/0074277 A1 | 4/2006 | Yoshida |
| 2006/0100480 A1 | 5/2006 | Ewers et al. |
| 2006/0189845 A1 | 8/2006 | Maahs et al. |
| 2006/0191975 A1 | 8/2006 | Adams et al. |
| 2006/0247662 A1 | 11/2006 | Schwartz et al. |
| 2006/0264706 A1 | 11/2006 | Piskun |
| 2007/0005093 A1 | 1/2007 | Cox |
| 2007/0021778 A1 | 1/2007 | Carly |
| 2007/0255207 A1 | 11/2007 | Hangai et al. |
| 2007/0287886 A1 | 12/2007 | Saadat |
| 2007/0287889 A1 | 12/2007 | Mohr |
| 2007/0293724 A1 | 12/2007 | Saadat et al. |
| 2008/0045842 A1 | 2/2008 | Furnish |
| 2008/0051629 A1 | 2/2008 | Sugiyama et al. |
| 2008/0058590 A1 * | 3/2008 | Saadat ............... A61B 1/00085 606/198 |
| 2008/0132835 A1 | 6/2008 | Nagamatsu et al. |
| 2008/0161645 A1 | 7/2008 | Goldwasser et al. |
| 2008/0188868 A1 | 8/2008 | Weitzner et al. |

(56) References Cited

U.S. PATENT DOCUMENTS

| | | | |
|---|---|---|---|
| 2008/0228209 A1 | 9/2008 | DeMello et al. | |
| 2008/0249534 A1 | 10/2008 | Gruber et al. | |
| 2008/0262492 A1 | 10/2008 | Lee | |
| 2008/0269557 A1* | 10/2008 | Marescaux | A61B 1/008 600/106 |
| 2008/0269559 A1 | 10/2008 | Miyamoto et al. | |
| 2008/0275300 A1* | 11/2008 | Rothe | A61B 1/05 600/129 |
| 2008/0300454 A1 | 12/2008 | Goto | |
| 2009/0018500 A1 | 1/2009 | Carter et al. | |
| 2009/0030369 A1 | 1/2009 | Nagamatsu et al. | |
| 2009/0149716 A1 | 6/2009 | Diao et al. | |
| 2009/0156996 A1 | 6/2009 | Milsom et al. | |
| 2009/0287046 A1 | 11/2009 | Yamatani | |
| 2009/0312645 A1 | 12/2009 | Weitzner et al. | |
| 2010/0010296 A1 | 1/2010 | Piskun | |
| 2010/0049137 A1 | 2/2010 | Fischer, Jr. | |
| 2010/0106240 A1 | 4/2010 | Duggal et al. | |
| 2010/0152590 A1 | 6/2010 | Moore et al. | |
| 2011/0065985 A1 | 3/2011 | Wehrheim | |
| 2011/0077498 A1 | 3/2011 | McDaniel | |
| 2011/0160538 A1 | 6/2011 | Ravikumar et al. | |
| 2011/0172491 A1 | 7/2011 | Piskun et al. | |
| 2011/0224494 A1 | 9/2011 | Piskun et al. | |
| 2011/0245858 A1 | 10/2011 | Milsom et al. | |
| 2011/0306832 A1 | 12/2011 | Bassan et al. | |
| 2012/0053485 A1 | 3/2012 | Bloom | |
| 2012/0083797 A1 | 4/2012 | Cabrera et al. | |
| 2012/0095498 A1 | 4/2012 | Stefanchik et al. | |
| 2012/0109178 A1 | 5/2012 | Edwards et al. | |
| 2012/0165604 A1 | 6/2012 | Stokes et al. | |
| 2013/0090527 A1 | 4/2013 | Axon | |
| 2013/0172828 A1 | 7/2013 | Kappel et al. | |
| 2013/0192116 A1 | 8/2013 | Elftmann, Jr. | |
| 2013/0274553 A1* | 10/2013 | Piskun | A61B 1/00154 600/114 |
| 2013/0274556 A1 | 10/2013 | Nearman et al. | |
| 2013/0317303 A1 | 11/2013 | Deshmukh et al. | |
| 2013/0324795 A1 | 12/2013 | Nakajima et al. | |
| 2014/0142393 A1* | 5/2014 | Piskun | A61B 1/00085 600/206 |
| 2014/0316379 A1 | 10/2014 | Sonderegger et al. | |
| 2015/0150436 A1 | 6/2015 | Cornhill et al. | |
| 2015/0157192 A1* | 6/2015 | Piskun | A61B 1/00085 600/114 |
| 2015/0265268 A1 | 9/2015 | Diao et al. | |
| 2015/0265818 A1 | 9/2015 | Piskun et al. | |
| 2015/0272564 A1* | 10/2015 | Piskun | A61B 1/00085 600/114 |
| 2015/0351890 A1 | 12/2015 | Levin et al. | |
| 2016/0038172 A1 | 2/2016 | Cox | |
| 2016/0081702 A1 | 3/2016 | Kan et al. | |
| 2016/0106466 A1 | 4/2016 | Gruber et al. | |
| 2016/0157843 A1 | 6/2016 | Dickson et al. | |
| 2016/0374658 A1* | 12/2016 | Piskun | A61B 1/00 600/204 |
| 2018/0228362 A1* | 8/2018 | Reydel | A61B 1/32 |

FOREIGN PATENT DOCUMENTS

| | | |
|---|---|---|
| CN | 201200436 Y | 3/2009 |
| CN | 102018493 A | 4/2011 |
| CN | 102695541 A | 9/2012 |
| CN | 103340679 A | 10/2013 |
| CN | 104135972 A | 11/2014 |
| CN | 100462044 C | 12/2016 |
| EP | 1588670 A1 | 10/2005 |
| EP | 2512577 A2 | 10/2012 |
| GB | 2365340 A | 2/2002 |
| JP | S63292935 A | 11/1988 |
| JP | H08317928 A | 12/1996 |
| JP | H08336538 A | 12/1996 |
| JP | 2533732 Y2 | 4/1997 |
| JP | H1028691 A | 2/1998 |
| JP | 2000166936 A | 6/2000 |
| JP | 2000325303 A | 11/2000 |
| JP | 2001527429 A | 12/2001 |
| JP | 2004154485 A | 6/2004 |
| JP | 2004529708 A | 9/2004 |
| JP | 2005046274 A | 2/2005 |
| JP | 2007511247 A | 5/2007 |
| JP | 2008528239 A | 7/2008 |
| JP | 2008536552 A | 9/2008 |
| JP | 2009523054 A | 6/2009 |
| JP | 2009279406 A | 12/2009 |
| JP | 2010511440 A | 4/2010 |
| JP | 2011072782 A | 4/2011 |
| JP | 2012075908 A | 4/2012 |
| JP | 2013514827 A | 5/2013 |
| JP | 2015525109 A | 9/2015 |
| WO | 9101773 A1 | 2/1991 |
| WO | 9635469 A1 | 11/1996 |
| WO | 9640347 A1 | 12/1996 |
| WO | 03000139 A1 | 1/2003 |
| WO | 2004103430 A2 | 12/2004 |
| WO | 2006110275 A2 | 10/2006 |
| WO | 2007081601 A2 | 7/2007 |
| WO | 2008011163 A2 | 1/2008 |
| WO | 2009059296 A1 | 5/2009 |
| WO | 2009076176 A1 | 6/2009 |
| WO | 2009117696 A1 | 9/2009 |
| WO | 2011084616 A2 | 7/2011 |
| WO | 2012068048 A1 | 5/2012 |
| WO | 2012114569 A1 | 8/2012 |
| WO | 2013050880 A2 | 4/2013 |
| WO | 2013192116 A1 | 12/2013 |
| WO | 2014164661 A1 | 10/2014 |
| WO | 2014200737 A1 | 12/2014 |
| WO | 2015026968 A1 | 2/2015 |
| WO | 2015191125 A1 | 12/2015 |

OTHER PUBLICATIONS

European Search Report dated Jun. 1, 2014 for International Application No. PCT/US2014/040429.
European Search Report dated May 3, 2011 for European Patent Application No. 06789411.3.
International Preliminary Report on Patentability dated Jun. 28, 2012 for International Application No. PCT/US2010/060802.
International Search Report and Written Opinion dated May 6, 2016 for International Application No. PCT/US2016/016911.
International Search Report and Written Opinion dated May 9, 2018, for PCT/US17/68991 11 pages.
International Search Report and Written Opinion for application No. PCT/US2014/04029, dated Aug. 1, 2014, 11 pages.
International Search Report and Written Opinion for International Application No. PCT/US18/14388, dated Jun. 19, 2018, 9 pages.
International Search Report and Written Opinion for International Application No. PCT/US18/21779, dated Jun. 14, 2018, 10 pages.
International Search Report and Written Opinion for International Application No. PCT/US2013/046200, dated Sep. 23, 2013, 11 pages.
International Search Report and Written Opinion for International Application No. PCT/US2016/031355, dated Sep. 23, 2016, 17 pages.
International Search Report and Written Opinion for PCT application No. PCT/US17/50685, dated Dec. 14, 2017 (16 pages).
International Search Report and Written Opinion for PCT/US10/60802, dated Aug. 24, 2011, 12 pages.
International Search Report and Written Opinion dated Jun. 20, 2007 for International Application No. PCT/US06/30464, 6 pages.
Letter from Jeffrey M. Chamberlain, Senior Principal at Kacvinsky Daisak Bluni pllc to Michael J. Rye, Esq. c/o Cantor Colburn, LLP, dated Nov. 13, 2018, 3 pages.
Letter from Kurt W. Lockwood, Principal at Kacvinsky Daisak Bluni pllc, to Philip G. Hampton, II c/o Haynes and Boone, LLP dated Nov. 9, 2018, 16 pages.
Letter from Michael J. Rye, Partner at Cantor Colburn LLP to Jeffrey M. Chamberlain at Kacvinsky Daisak Bluni PLLC, dated Aug. 28, 2018, 2 pages.

(56) References Cited

OTHER PUBLICATIONS

Letter from Michael J. Rye, Partner at Cantor Colburn LLP to Michael Mahoney, CEO at Boston Scientific Corporation, dated Oct. 17, 2017, 3 pages.

Letter from Philip G. Hampton, II at Haynes and Boone, LLP to Kurt W. Lockwood, Esq. at Kacvinsky Daisak Bluni PLLC, dated Nov. 16, 2018, 2 pages.

*Oleg Shikhman* vs. *Bobcat Endoscopy, LLC (F/K/A/ LumenR LLC) and Gregory Piskun, M.D.* Complaint, filed on Oct. 17, 2017, at Judicial District of Fairfield at Bridgeport, 25 pages.

*Oleg Shikhman* vs. *Bobcat Endoscopy, LLC (F/K/A/ LumenR LLC) and Gregory Piskun, M.D.* Reply to Affirmative Defenses, Matters in Avoidance and Answer to Counterclaims, Docket No. X03-HHD-CV17-6087023-S, dated Dec. 12, 2018, 19 pages.

*Oleg Shikhman* vs. *Bobcat Endoscopy, LLC (F/K/A/ LumenR LLC) and Gregory Piskun, M.D.*, Answer, Special Defenses and Counterclaims, Docket No. HHD-CV-608 7023-S, dated Sep. 13, 2018, 23 pages.

*Oleg Shikhman* vs. *Bobcat Endoscopy, LLC (F/K/A/ LumenR LLC) and Gregory Piskun, M.D.*, First Amended Answer, Affirmative Defenses and Counterclaims, Docket No. X03-HHD-CV17-6087023-S, dated Nov. 9, 2018, 24 pages.

*Sergey Kantsevoy* v. *LumenR LLC Complaint*, Civil Action No. 17-359, filed Feb. 7, 2017, 18 pages.

*Sergey Kantsevoy* v. *LumenR LLC*, Answer, Affirmative Defenses and Counterclaims, Civil Action No. 17-cv-359 (ELH), filed Feb. 28, 2017, 25 pages.

*Sergey Kantsevoy* v. *LumenR LLC*, Dr. Sergey Kantsevoy's Answer to LumenR LLC's Counterclaims, Civil Action No. 17-359 (ELH), filed Mar. 17, 2017, 8 pages.

The Extended PCT Search Report Application No. PCT/US2016/031355 dated Jul. 18, 2016.

Written Opinion dated Jun. 20, 2007 for International Application No. PCT/US06/30464.

European Search Report for the European Patent Application No. EP19214960, dated Apr. 17, 2020, 6 pages.

European Search Report for the European Patent Application No. EP20151480, dated Jul. 10, 2020, 9 pages.

*Oleg Shikhman* v. *Bobcat Endscopy LLC, et al.*, Memorandum of Decision, filed Oct. 31, 2019, 22 pages (p. 1, line 15—p. 2, line 3; p. 2, lines 7-8, p. 7, lines 4-6; p. 8, lines 3-13; p. 10, line 4—p. 11, line 9; p. 18, line 5—p. 19, line 2; p. 18. footnote 15.).

Extended European Search Report and Written Opinion for the European Patent Application No. EP19214866, dated Apr. 20, 2020, 10 pages.

International Search Report and Written Opinion for the International Patent Application No. PCT/US2020/063710, dated Mar. 30, 2021, 15 pages.

\* cited by examiner

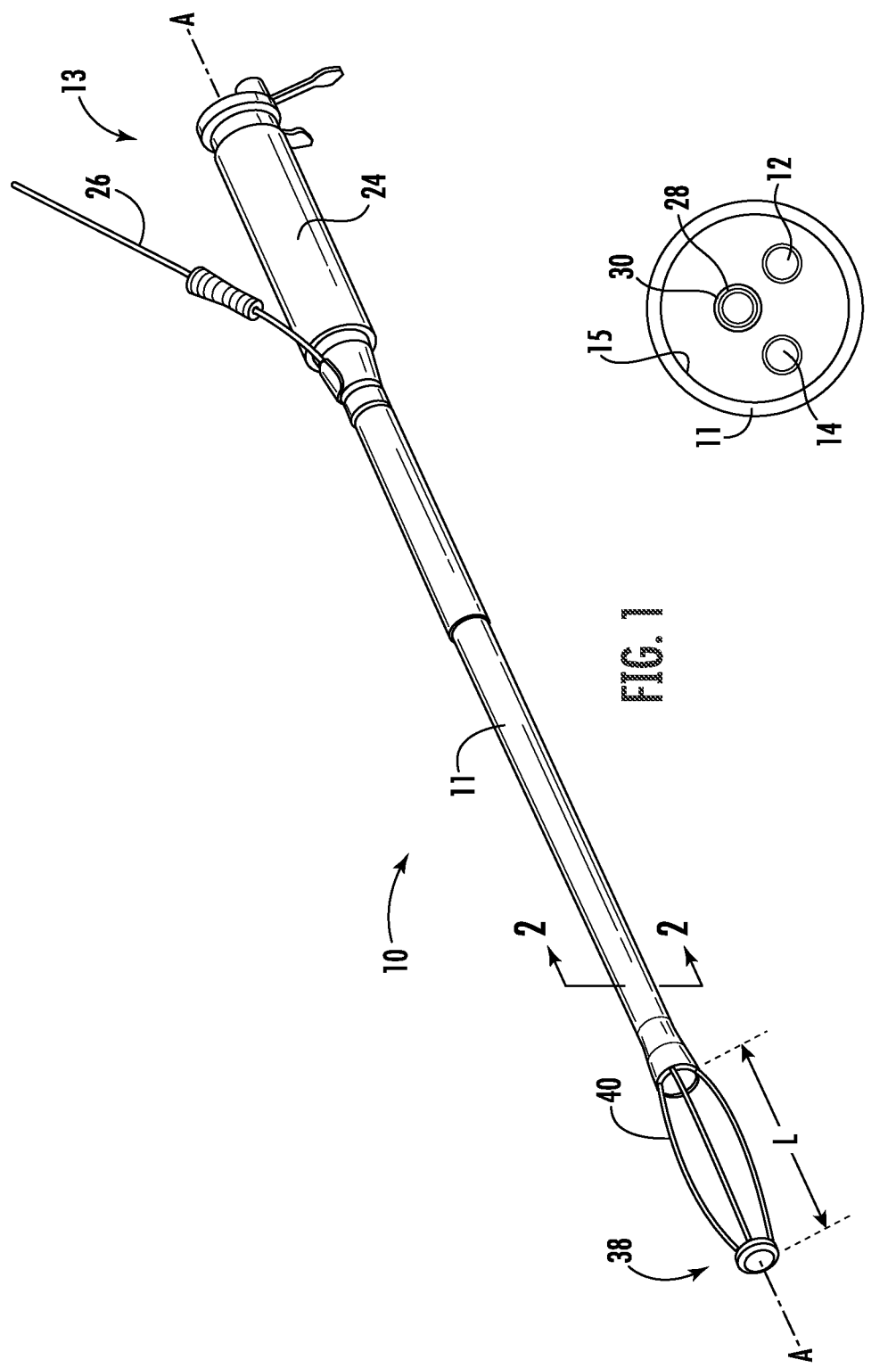

DEVICES, SYSTEMS, AND METHODS FOR MINIMALLY INVASIVE SURGERY IN A BODY LUMEN

CROSS REFERENCE TO RELATED

The present application is a non-provisional of, and claims the benefit of priority under 35 U.S.C. § 119 to, U.S. Provisional Application Ser. No. 62/947,659, filed Dec. 13, 2019, the disclosures of which are herein incorporated herein by reference in their entirety.

FIELD

The present disclosure relates generally to the field of medical devices for operatively treating gastrointestinal disorders endoscopically in a stable, yet dynamic operative environment, and in a minimally invasive manner. In particular, the present disclosure relates to medical devices, systems and methods for expanding a body lumen to provide a customizable working space for maneuverability of endoscopic instruments.

BACKGROUND

Endoscopic procedures involving the gastrointestinal system can be less invasive than traditional procedures and may enable expansion of a stable, working space adjacent to the target tissues that could otherwise collapse around the target lesion or defect during an operative treatment. A better expanded, stable and optimally configured working space enables instruments and endoscope to be independently manipulated and visualized around the target tissue.

It is with the above considerations in mind that the improvements of the present disclosure may be useful.

SUMMARY

The present disclosure, in its various aspects, relates to tissue devices and methods for providing a working space within a body lumen.

A system is disclosed for performing minimally invasive procedures in a body lumen of a patient. The system may include a flexible tubular member having a first lumen for receiving an endoscope, and an adjustable cage disposed at a distal end of the flexible tubular member. The adjustable cage can include a plurality of flexible elements that are independently and selectively movable laterally outwardly to move a side wall of the body lumen outwardly to increase visualization and a working space within the body lumen. The system may include a handle having a plurality of actuators movably disposed with respect to a body portion of the handle, where each of the plurality of actuators is coupled to a selected one of the plurality of flexible elements such that moving one of the plurality of actuators extends or retracts the coupled flexible element to adjust the shape of the adjustable cage.

In some embodiments, the plurality of flexible elements are fixedly coupled between the plurality of actuators and a cap member disposed at a distal end of the system. In some embodiments, the plurality of flexible elements comprise first, second, third and fourth flexible elements. In some embodiments, the plurality of flexible elements comprise wires. In some embodiments, the adjustable cage forms a working space therein. The system may further include a cap member coupled to distal ends of the plurality of flexible elements.

In some embodiments, a shape of the adjustable cage is selectively adjustable by actuating one or more of the plurality of actuators to orient the cap member toward a targeted lesion. In some embodiments, the cap member comprises an opening sized and configured to receive an endoscope therethrough. In some embodiments, the cap member comprises one or more slits radiating from the opening. In some embodiments, the cap member comprises a lateral slit between proximal and distal ends of the cap member for allowing the endoscope to laterally disengage from the cap member through the lateral slit.

The system may further include a connecting member disposed between a distal end of the flexible tubular member and a proximal end of the cap member, the connecting member including a flexible braid element. The system may further include first and second working channels coupled between first and second lumens of the flexible tubular member and the cap member. In some embodiments, the adjustable cage has a retracted configuration and an extended configuration, and a length of the adjustable cage in the retracted configuration is smaller than the length of the adjustable cage in the extended configuration. In some embodiments, the adjustable cage has a contracted configuration and an expanded configuration, and an outer dimension of the adjustable cage in the contracted configuration is smaller than the outer dimension of the adjustable cage in the expanded configuration. In some embodiments, the flexible tubular member comprises a multilayer construction having layers selected from the list consisting of a polymer layer, a braid layer, and a helical coil layer.

A system is disclosed for performing minimally invasive procedures in a body lumen of a patient. The system can include a flexible tubular member having a first lumen for receiving an endoscope, and an adjustable cage disposed at a distal end of the flexible tubular member. The adjustable cage can include a plurality of flexible elements that are independently and selectively movable laterally outwardly to move a side wall of the body lumen outwardly to increase visualization and a working space within the body lumen. The system can include a handle having a plurality of actuators movably disposed with respect to a body portion of the handle, each of the plurality of actuators coupled to a selected one of the plurality of flexible elements such that moving one of the plurality of actuators extends or retracts the coupled flexible element to adjust the shape of the adjustable cage.

In some embodiments, the plurality of flexible elements are fixedly coupled between the plurality of actuators and a cap member disposed at a distal end of the system. In some embodiments, the plurality of flexible elements comprise first, second, third and fourth flexible elements. In some embodiments, the plurality of flexible elements comprise wires. In some embodiments, the adjustable cage forms a working space therein.

The system may further include a cap member coupled to distal ends of the plurality of flexible elements. In some embodiments, a shape of the adjustable cage is selectively adjustable by actuating one or more of the plurality of actuators to orient the cap member toward a targeted lesion. In some embodiments, the cap member comprises an opening sized and configured to receive an endoscope therethrough. In some embodiments, the cap member comprises one or more slits radiating from the opening.

In some embodiments, the cap member comprises a lateral slit between proximal and distal ends of the cap member for allowing the endoscope to laterally disengage from the cap member through the lateral slit. The system may further include a connecting member disposed between a distal end of the flexible tubular member and a proximal end of the cap member, the connecting member including a flexible braid element. The system may further include first and second working channels coupled between first and second lumens of the flexible tubular member and the cap member.

In some embodiments, the adjustable cage has a retracted configuration and an extended configuration, and a length of the adjustable cage in the retracted configuration is smaller than the length of the adjustable cage in the extended configuration. In some embodiments, the adjustable cage has a contracted configuration and an expanded configuration, and an outer dimension of the adjustable cage in the contracted configuration is smaller than the outer dimension of the adjustable cage in the expanded configuration.

In some embodiments, the flexible tubular member comprises a multilayer construction having layers selected from the list consisting of a polymer layer, a braid layer, and a helical coil layer. In some embodiments, the plurality of flexible elements are disposed through openings in a distal end of the flexible tubular member. In some embodiments, the openings have axes, each of said axes being oriented at an oblique angle with respect to a longitudinal axis of the flexible tubular member.

A method is disclosed for performing a minimally invasive procedure in a body lumen of a patient. The method can include: inserting a flexible tubular member into a body lumen and navigating an adjustable cage of the flexible tubular member toward a targeted lesion, the adjustable cage comprising a plurality of flexible element; manipulating at least one actuator of a plurality of actuators to extend or retract one of a plurality of flexible elements of the adjustable cage to selectively adjust a shape of the adjustable cage dependent upon a position of the targeted lesion, wherein each one of the plurality of actuators is individually associated with one of the plurality of flexible elements; and inserting a working instrument through the flexible tubular member to perform an operation on a lesion adjacent to the adjustable cage.

The method may further include inserting an endoscope through the flexible tubular member and extending the endoscope through an opening in a cap member of the adjustable cage to visualize a portion of the body lumen beyond a distal end of the adjustable cage. The method may further include performing an operation on a lesion to comprises performing an operation on a lesion disposed distal to the cap member.

BRIEF DESCRIPTION OF THE DRAWINGS

Non-limiting embodiments of the present disclosure are described by way of examples with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 1 illustrates a minimally invasive surgical system according to an embodiment of the present disclosure.

FIG. 2 is a cross-section view of a portion of the system of FIG. 1, taken alone line 2-2 of FIG. 1.

DETAILED DESCRIPTION

Figure 3:
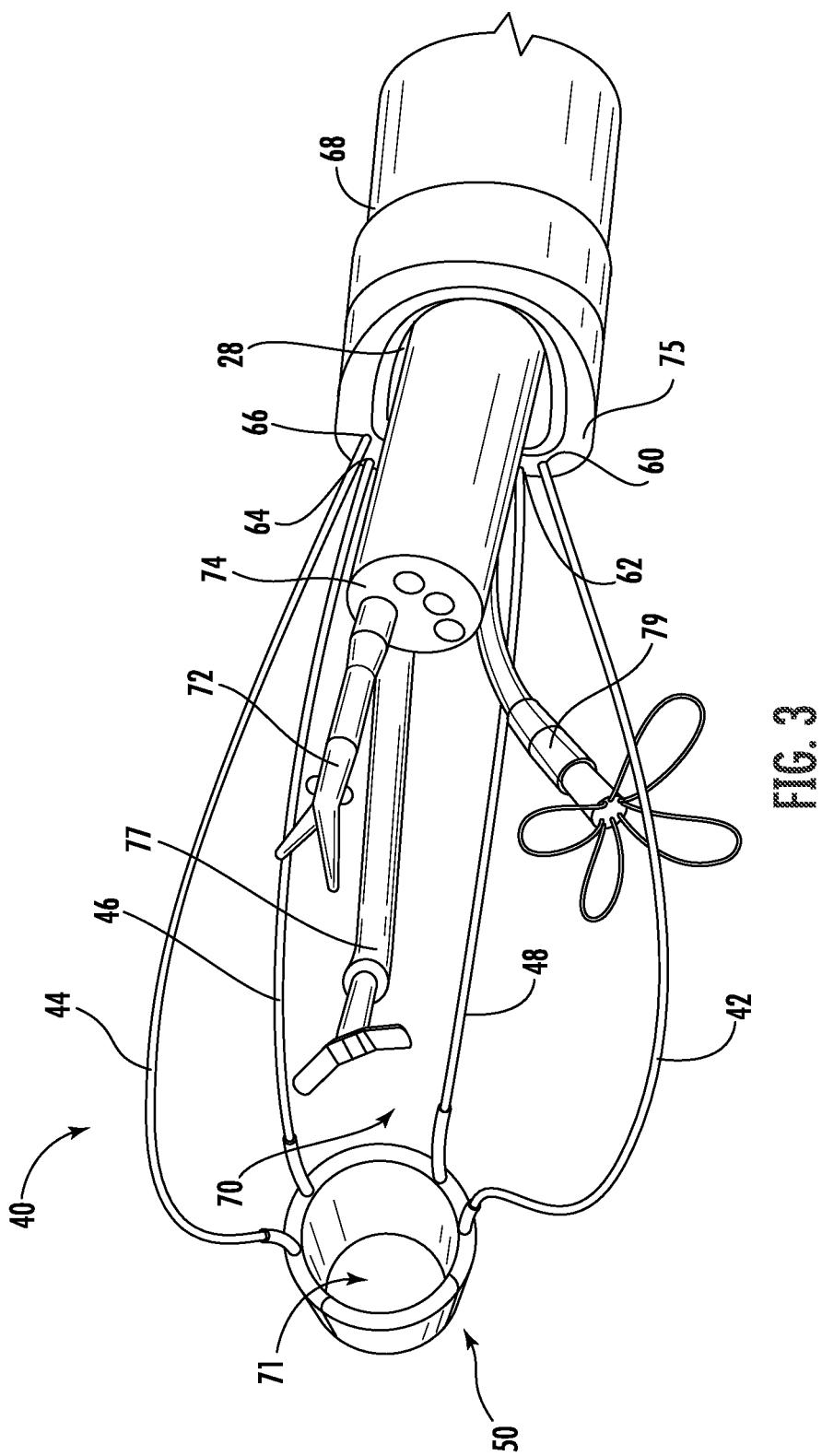
FIG. 3 is an isometric view of an adjustable cage of the system of FIG. 1, the adjustable cage being in an expanded configuration.

The present disclosure is not limited to the particular embodiments described. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure may be described with specific reference to medical devices and systems, it should be appreciated that such medical devices and systems may be used in a variety of medical procedures that require grasping, retracting, and resecting tissue in GI tract. The disclosed medical devices and systems may also be inserted via different access points and approaches, e.g., percutaneously, endoscopically, laparoscopically, or combinations thereof.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, "proximal end" refers to the end of a device that lies closest to the medical professional along the device when introducing the device into a patient, and "distal end" refers to the end of a device or object that lies furthest from the medical professional along the device during implantation, positioning, or delivery.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

All numeric values are herein assumed to be modified by the term "about," whether or not explicitly indicated. The term "about," in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment," "some embodiments," "other embodiments," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

FIGS. 1 and 2 illustrate an embodiment of a system 10 for performing minimally invasive surgery in a body lumen. The system 10 may include a flexible tubular member 11 having a proximal end 13 including a handle 24, and a distal portion 38 including an adjustable cage 40 for positioning within the body lumen adjacent a targeted lesion.

The flexible tubular member 11 may be configured to receive one or more instruments therethrough, and in some embodiments the flexible tubular member 11 can have multiple lumens 12, 14 to receive such instruments. The flexible tubular member 11 can also include a lumen 28 configured and dimensioned to receive an endoscope 30, which may be an articulating endoscope (including but not limited to an endoscope, bronchoscope, colonoscope, catheter delivery system, and the like), as well as first and second lumens 12, 14, which in some non-limiting example embodiments comprise fluoropolymer (Teflon) tubing. As will be appreciated, any number of lumens can be provided within the flexible tubular member 11, at any position, to provide the user with flexibility in determining a desired instrument insertion position based on the position of the lesion within the body lumen.

As mentioned, flexible tubular member 11 includes a handle 24 at the proximal portion 13. As will be described, the handle 24 may have multiple actuation elements to enable a user to selectively adjust a size, shape and/or position of the adjustable cage 40. Flexible tubular member 11 can also include tubing 26 which may be an insufflation port for supplementing insufflation gas provided by the endoscope 30.

Adjustable cage 40 is shown in a collapsed configuration in FIG. 1. As will be appreciated, the adjustable cage 40 may be positioned in the collapsed configuration when the flexible tubular member 11 is inserted into the body lumen. Once the adjustable cage 40 is navigated through the body lumen and positioned adjacent to a targeted lesion, the user may selectively expand the adjustable cage into an expanded configuration. In some embodiments the expansion of the adjustable cage can be selectively asymmetric to maximize space for a tool and an endoscope to visualize a target tissue and treat the target tissue from outside the patient in a minimally invasive manner. When expanded, the adjustable cage 40 outwardly engages one or more walls of the body lumen to expand the body lumen, providing an increased working space to enable tools extended through the flexible tubular member 11 to access a lesion within the body lumen. As will be appreciated, providing an increased working space enables the instruments inserted into the space to have a wider range of motion for engaging a lesion than would otherwise be available in the absence of such expansion.

The flexible tubular member 11 may be sufficiently flexible, and of sufficiently small girth, to navigate through long, tortuous paths associated with body lumens so that lesions disposed in far reaches of the body lumens can be reached and removed using the system 10. As can be appreciated, the flexures required to traverse such lengths of body lumens can cause the distal portion 38 of the flexible tubular member 11 to bias to an outer section of the lumen when the distal portion encounters a particular curvature of the lumen. This can make it difficult to move the flexible tubular member 11 past such curvatures to reach a targeted lesion. Such long tortuous paths can also result in kinking or binding of moving components and mechanisms associated with the flexible tubular member 11, which can inhibit some or all the functionality of the system 10. As will be described, the system 10 according to disclosure includes features to facilitate movement of the flexible tubular member 11 around such curvatures.

In addition to enabling the flexible tubular member 11 to navigate the body lumen, it is often desirable to apply torque to the flexible tubular member 11 to rotate the distal portion 38 to obtain a desired alignment of the adjustable cage 40 and/or the endoscope 30 or the instruments. Such rotational positioning enables tasks such as visualization, retraction, space creation, and/or resection to be achieved. As will be appreciated, transmitting torque along the entire length of a flexible tubular member can be difficult in a long device that has multiple bends along its length. As will also be described, the system 10 according to the disclosure includes features that enhance the torque-transmission capacity of the flexible tubular member 11.

Figure 4:
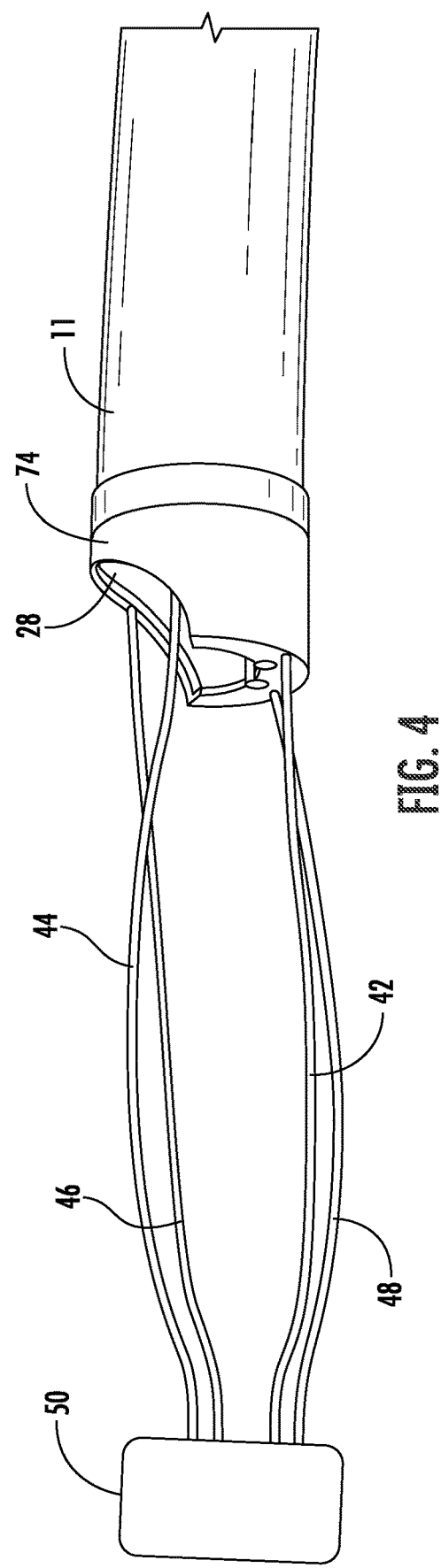
FIG. 4 is a side view of the adjustable cage of the system of FIG. 1, the adjustable cage being an unexpanded, delivery, configuration.
Figure 5:
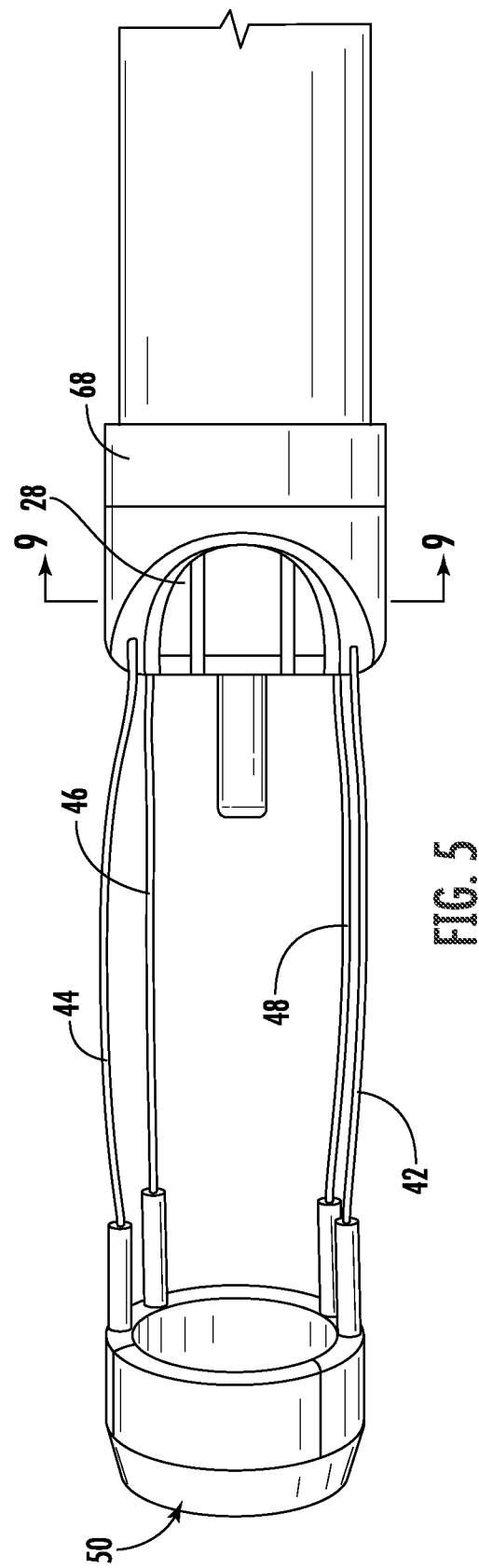
FIG. 5 is a top view of the adjustable cage of the system of FIG. 1, the adjustable cage being an unexpanded, delivery, configuration.

Referring now to FIGS. 3-5, an adjustable cage 40 may comprise a plurality of flexible elements 42, 44, 46, 48, that can be independently adjustable to enable a user to selectively adjust a size and shape of the adjustable cage. In the illustrated embodiment, the plurality of members 42, 44, 46, 48 comprise a plurality of wires that form a cage. It will be appreciated that although the illustrated embodiment includes four flexible elements, greater or fewer flexible elements can be employed to form the adjustable cage 40. In addition, although the illustrated embodiment shows the flexible elements as being wires, the flexible elements can be made from any structural elements that can provide the desired functionality as will be described herein.

As shown, the plurality of flexible elements 42, 44, 46, 48 each have a distal end 42a, 44a, 46a, 48a that is fixedly coupled to a cap member 50. Proximal ends 42b, 44b, 46b, 48b (44b only shown in FIG. 7) of the plurality of flexible elements 42, 44, 46, 48 are coupled to respective actuators 52, 54, 56, 58 (FIG. 6) associated with handle 24. As will be described, the flexible elements 42, 44, 46, 48 can be disposed within the flexible tubular member 11 and exit through openings 60, 62, 64, 66 adjacent a distal end 68 of the flexible tubular member 11 (FIG. 3). The plurality of flexible elements 42, 44, 46, 48 can be independently extended and retracted with respect to the distal end 68 of the flexible tubular member 11 by individually actuating the respective actuators 52, 54, 56, 58 of the handle 24. In this manner, the shape of the adjustable cage 40 can be customized in order to obtain a working space 70 that is shaped so that instruments inserted into the working space can access a targeted lesion.

FIG. 3 shows the adjustable cage 40 in an expanded configuration. In the illustrated configuration two of the flexible elements 42, 44 are extended while the other two flexible elements 46, 48 are either maintained in place or retracted. This results in the adjustable cage being bowed on one side to provide a desired asymmetrical expansion of the body lumen on that side of the adjustable cage 40. Since the plurality of flexible elements 42, 44, 46, 48 are independently extendable/retractable, the adjustable cage 40 is infinitely adjustable by the user to obtain a working space 70 that has a desired shaped, depending on the shape of the body lumen and the position of the targeted lesion. This provides the user with an enhanced array of options for accessing a lesion using one or more instruments and an endoscope disposed through the flexible tubular member 11.

As can be seen in FIG. 3, endoscope 30 is extendible through lumen 28 into working space 70 formed by the adjustable cage 40. Also extendable into the working space 70 are a first instrument 72 which can extend from a working channel 74 in the endoscope 30, a second instrument 77 which can extend from the first lumen 12 (FIG. 2) in the flexible tubular member 11, and a third instrument 79 which can extend from the second lumen 14 (FIG. 2) in the flexible tubular member 11. As will be appreciated, the disclosed arrangement can enable a variety of visualization and tissue manipulation functions to be performed on a targeted lesion.

In some non-limiting example embodiments, the plurality of flexible elements 42, 44, 46, 48 are wires made from nickel titanium (e.g., super-elastic or shape memory metal such as Nitinol) that are rigidly coupled at distal ends 42a, 44a, 46a, 48a to the cap member 50. In non-limiting example embodiments, the wires have diameters from 0.010-0.080 inches. The cap member 50 may be made from any appropriate material, a non-limiting example listing of which includes polycarbonate, ABS, PeBax, polyamide, and polyethylene rigid plastic. The cap member 50 may also include an opening 71 sized to allow a tip of the endoscope to nest therein, for example, while the system 10 is being navigated through the body lumen. The opening 71 may also allow a portion of the endoscope 30 to pass therethrough to facilitate visualization of the body lumen and/or the targeted lesion using a visualization capability of the endoscope.

Figure 9:
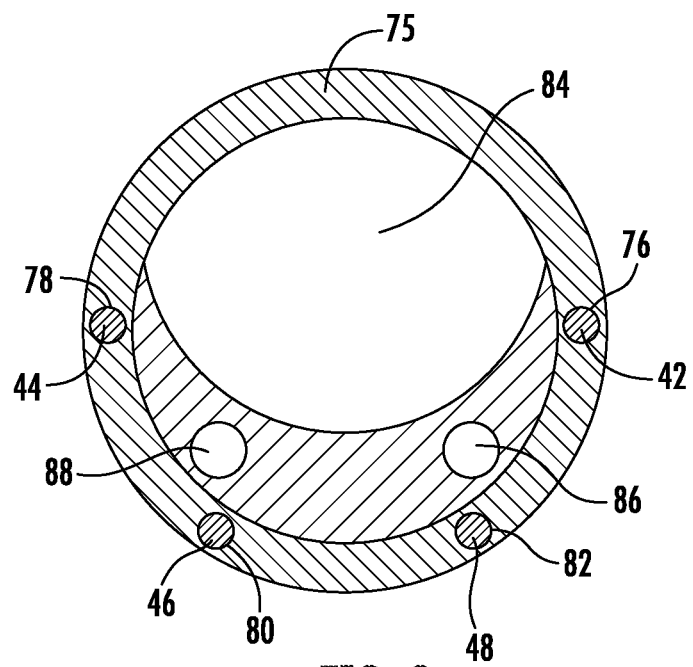
FIG. 9 is a cross-section view of a cap portion of the system of FIG. 1, taken alone line 9-9 of FIG. 5.

A cap member 75 may be disposed on or over the distal end 68 of the flexible tubular member 11. As shown in FIG. 9, the plurality of flexible elements 42, 44, 46, 48 are received through respective openings 76, 78, 80, 82 in the cap member 75. The cap member 75 can also include an opening 84 aligned with a portion of the lumen 28 in the flexible tubular member 11 for receiving the endoscope 30 therethrough, and respective openings 86, 88 aligned with the first and second lumens 12, 14 in the flexible tubular member 11 through which instruments and/or tool guides can extend. The cap member 75 can also include a window opening 77 (see FIGS. 4 and 5) lateral to the lumen opening 84 (FIG. 9) of the cap member 75 to facilitate lateral egress of the endoscope 30 from the flexible tubular member 11.

Figure 6:
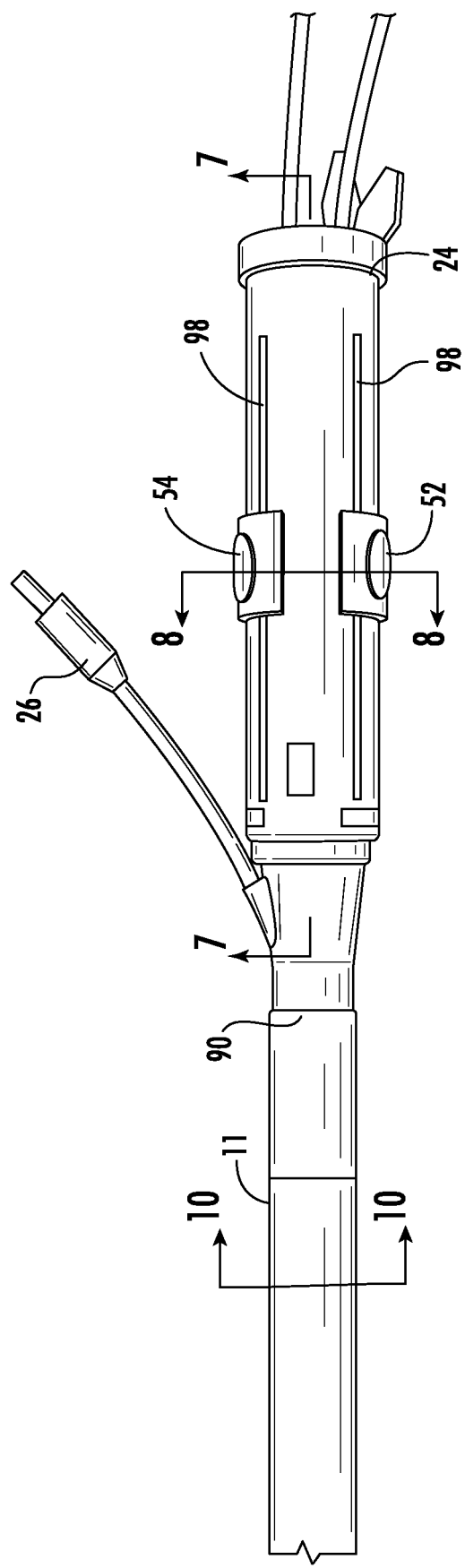
FIG. 6 is a side view of a handle portion of the system of FIG. 1.
Figure 7:
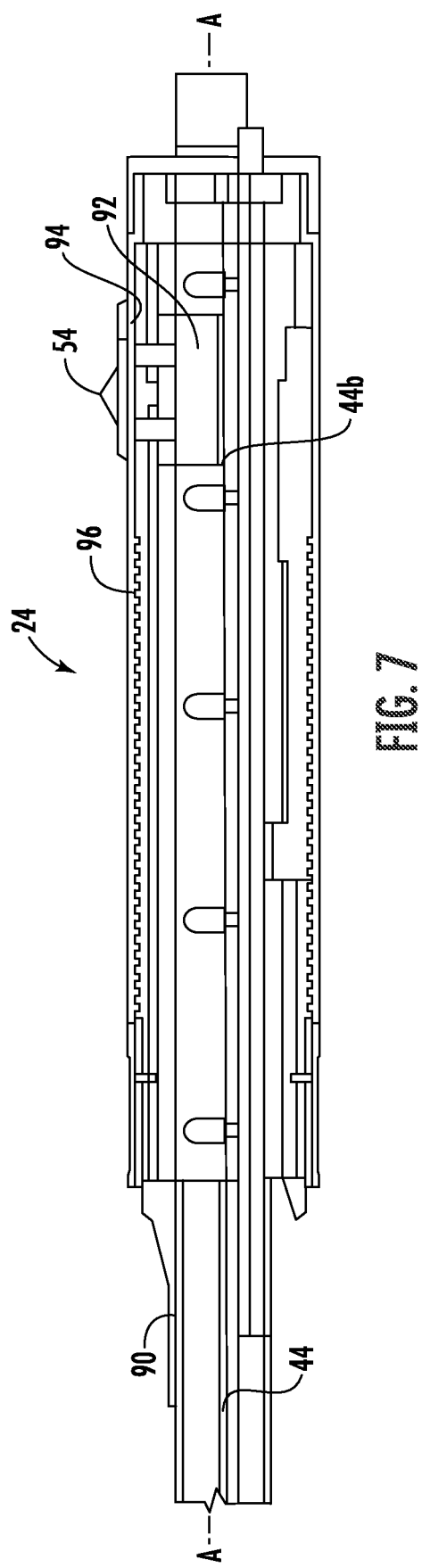
FIG. 7 is a cross-section view of the handle portion of FIG. 6, taken alone line 7-7 of FIG. 6.
Figure 8:
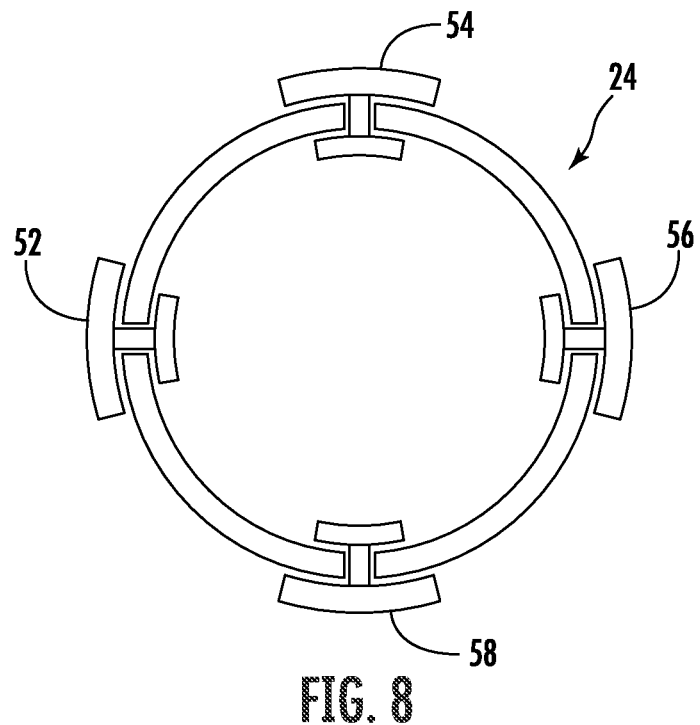
FIG. 8 is another cross-section view of the handle portion of FIG. 6, taken alone line 8-8 of FIG. 6.

Referring now to FIGS. 6-8, the handle 24 may be coupled to a proximal end 90 of the flexible tubular member 11. As mentioned, the handle 24 can include a plurality of actuators 52, 54, 56, 58, each of which may be coupled, directly or indirectly, to one of the plurality of flexible elements 42, 44, 46, 48. In the illustrated embodiment the plurality of actuators 52, 54, 56, 58 are slidably coupled to the handle 24 so that they can be selectively moved in directions parallel to the longitudinal axis A-A of the system 10. As will be described in greater detail, coupling each of the plurality of actuators 52, 54, 56, 58 to a single one of the plurality of flexible elements 42, 44, 46, 48 enables a user to selectively actuate one or more of actuators (e.g., sliding them toward or away from the adjustable cage 40) to independently move the flexible elements 42, 44, 46, 48 to adjust the size and/or shape of the adjustable cage 40. In some non-limiting example embodiments, two or more of the actuators 52, 54, 56, 58 could be coupled together to operate multiple wires simultaneously, if desired.

As shown in greater detail in FIG. 7, actuator 54 is operably connected to a flexible element (e.g., flexible element 44) via an element coupler 92. It will be appreciated that although this description will progress in relation to actuator 54, the same description will apply to the other actuators 52, 56, 58 associated with the handle 24. The actuator 54 can be reversibly engageable with the handle 24 such that the actuator 54 can be reversibly fixed in position relative to the handle 24. In some embodiments, the actuator 54 can be multi-positional, having a plurality of positions for extension and retraction of an associated flexible element (e.g., flexible element 44). In one non-limiting example embodiment, the actuator 54 can have a plurality of ratchet teeth 94 for engaging corresponding ratchet teeth 96 of the handle 24, to provide a plurality of positions for reversibly fixing the retractor in position during expansion or collapse of the retractor. The actuator 54 may be selectively locked with a spring-loaded plunger (not shown) which biases the ratchet teeth 94 of the actuator 54 into engagement with the ratchet teeth 96 of the handle 24 to hold the actuator 54 (and the associated flexible element 44) in a desired position. The user can push on the actuator to release the lock and slide the actuator 54 in either direction (i.e., toward or away from the adjustable cage 40 along axis A-A) to extend or retract the flexible element 44.

The handle 24 can be provided in any of a variety of shapes to achieve a desired ergonomic configuration for operation of the system by way of example, the actuator 54 can be configured as a finger-activated actuator on the handle 24 that slides back and forth through a slot 98 (FIG. 6) in the handle 24 to expand or collapse the retractor elements. An arrangement for dynamically adjusting or ratcheting the retractor position can be provided along the slot 98 to lock the position of the flexible elements in place when the associated actuator is not pressed.

As discussed, by enabling the individual flexible elements 42, 44, 46, 48 to be extended, retracted, or held in place via selective activation of one or more of the actuators 52, 54, 56, 58, the adjustable cage 40 can be lengthened (i.e., extended), shortened (i.e., retracted), and/or adjusted to achieve a variety of laterally expanded and contracted configurations. For example, the expansion of the adjustable cage can be selectively asymmetric to maximize space for a tool and an endoscope to visualize a target tissue and treat the target tissue from outside the patient in a minimally invasive manner.

Thus, in some embodiments the actuators 52, 54, 56, 58 can be moved between an extended position in which the adjustable cage 40 has a first length, and a retracted position in which the adjustable cage 40 has a second length smaller than the first length. In one non-limiting example embodiment the first length is from 5 cm to 15 cm, while the second length is from 4 cm to 0 cm. In some embodiments the user may configure the adjustable cage in the retracted and unexpanded configuration during navigation through the body lumen. Once the adjustable cage has been navigated through the body lumen and positioned adjacent to a targeted lesion, one or more of the actuators 52, 54, 56, 58 can be adjusted to configure the adjustable cage 40 in the extended and expanded configuration to provide access to the lesion by the endoscope 30 and one or more instruments.

In some embodiments, some or all of the flexible elements 42, 44, 46, 48 may be provided with a pre-determined curvature so that the resulting adjustable cage 40 is biased into a desired pre-determined shape. In some embodiments, the openings 76, 78, 80, 82 in the cap member 75 may have a desired orientation (e.g., they may be oriented at an oblique angle (e.g., up to and including 45-degrees) with respect to the longitudinal axis A-A of the system 10 so that the curvatures of the individual flexible elements 42, 44, 46, 48 are aligned with the trajectory of the openings, positioning the convexity of the flexible elements on the outside of the adjustable cage 40. In some embodiments, one or more openings 76, 78, 80, 82 in the cap member 75 may be oriented at oblique angles of from 1-45°, or from 5-30°, with respect to the longitudinal axis A-A of the system 10. In such embodiments, the adjustable cage 40 may form an overall convex "football" shape when the flexible elements 42, 44, 46, 48 are extended. In some example embodiments, rigid guide tubes may be embedded in the cap member 75 to provide a desired orientation to the flexible elements 42, 44, 46, 48. In some embodiments, convexity can be facilitated by pre-stressing and/or pre-shaping one or more of the flexible elements 42, 44, 46, 48. In other embodiments, convexity is implemented by extending one or more of the flexible elements 42, 44, 46, 48 while maintaining or shortening the length of other of the flexible elements to force the extended flexible elements into a bow shape.

During insertion of the system 10 into the body lumen, and while navigating the adjustable cage 40 to a target lesion, the actuators 52, 54, 56, 58 on the handle 24 can be moved within their respective slots 98 (FIG. 6) in a direction away from the adjustable cage 40. This can cause the associated flexible elements 42, 44, 46, 48 to retract, thereby shortening the adjustable cage 40 to assume the shortened, second length to facilitate advancement of the adjustable cage 40 around curves of the body lumen.

With the adjustable cage 40 configured to assume the shortened, second length, the adjustable cage 40 will have increased torsional stiffness (as compared to its torsional stiffness in the extended configuration), and can be more easily rotated to align the system 10 in a desired orientation with minimal twisting along the length of the flexible tubular member 11. In addition, during navigation through the body lumen, one or more of the flexible elements 42, 44, 46, 48 can be extended to provide the adjustable cage 40 with a curvature that matches a particular curvature of the lumen. This steerability, achieved through selective movement of individual actuators 52, 54, 56, 58 makes traversing such curves easier.

Once the adjustable cage 40 has been navigated within the body lumen to a desired position with respect to the targeted lesion, the actuators 52, 54, 56, 58 can be moved within their respective slots 98 to extend the length of the adjustable cage 40 to span the lesion so that a desired working space 70 can be achieved.

Figure 10:
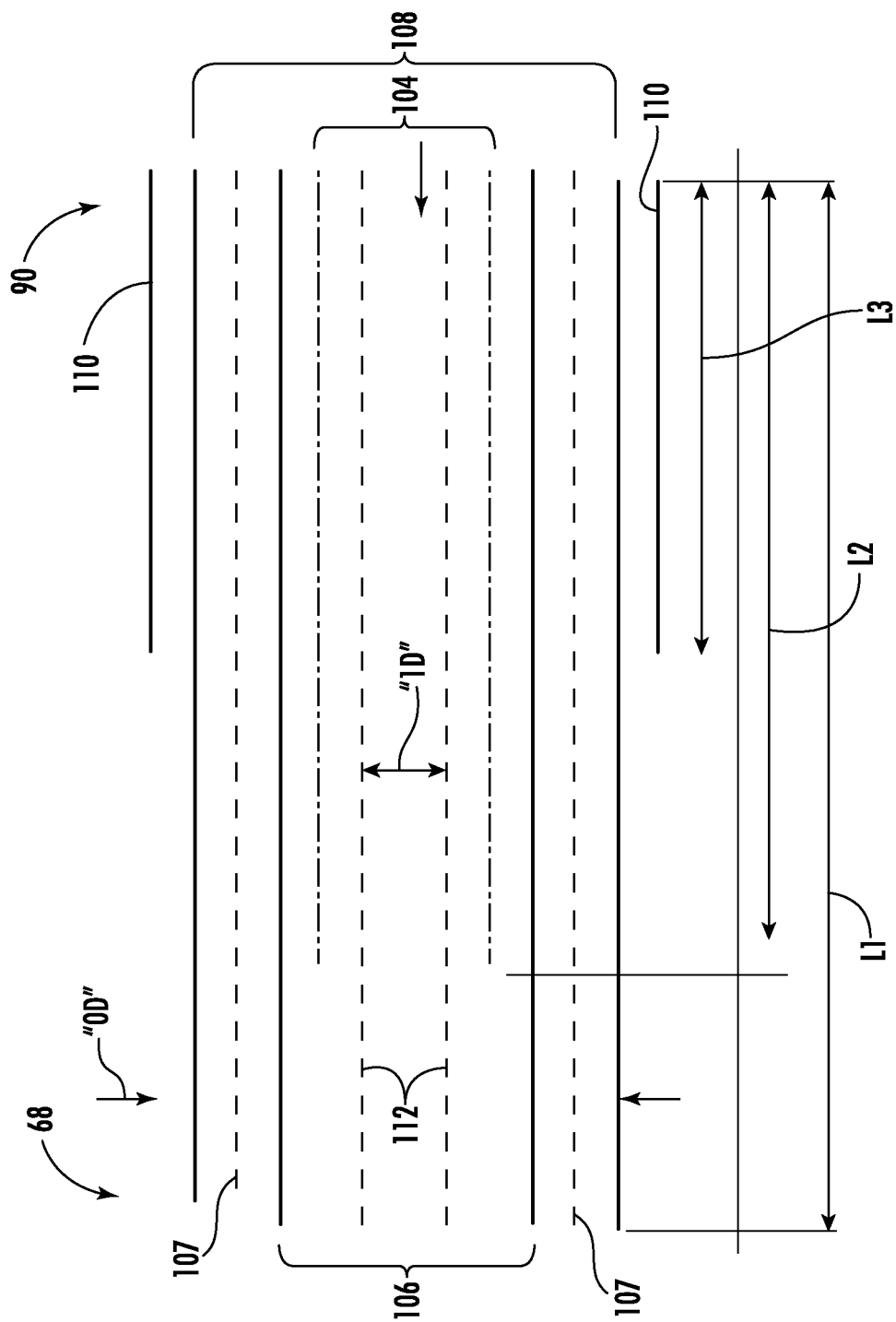
FIG. 10 is a cross-section view of the flexible tubular member of the system of FIG. 1, taken alone line 9-9 of FIG. 6.

As mentioned, the flexible tubular member 11 may have enhanced torsional stiffness, which can enable the flexible tubular member to be easily rotated to align the system 10 in a desired orientation, with minimal twisting along the length of the flexible tubular member. FIG. 10 illustrates an exemplary construction of the flexible tubular member 11.

In general, the flexible tubular member 11 comprises a multi-layer construction including one or more polymer layers and one or more reinforcing layers. In the illustrated embodiment, a first braid layer 102 is surrounded by a metal helical coil layer 104. The metal helical coil layer 104 is surrounded by a first polymer tubing layer 106. The first polymer tubing layer 106 is surrounded by a second braid layer 107. The second braid layer 107 is surrounded by a second polymer tubing layer 108, and a third polymer tubing layer 110 overlies the second polymer tubing layer 108.

The layers are assembled and subjected to heat sufficient to melt the first, second and third polymer tubing layers 106, 108, 110, such that they melt through the metal helical coil layer 104 and the first and second braid layers 102, 107, bonding the layers together and acting as a flexible matrix that holds the layers together.

The first braid layer 102, first polymer tubing layer 106, second braid layer 107 and second polymer tubing layer 108 may all be of the same length "L1", which in non-limiting example embodiments is 28-40 inches. The metal helical coil layer 104 may be of shorter length "L2", which in one non-limiting example embodiment is 18-30 inches. The third polymer tubing layer 110 may be of yet a shorter length "L3", which in non-limiting example embodiment is 11-23 inches. The outer diameter "OD" of the flexible tubular member 11 may, in non-limiting example embodiments, be 1.120 inches to 0.620 inches. The inner diameter "ID" of the flexible tubular member 11 may, in non-limiting example embodiments, be 0.900 inches to 0.500 inches.

The first, second and third polymer tubing layers 106, 108, 110 may be an elastomeric material such as Polyvinyl Chloride (PVC) or polyurethane, with a durometer of from 25-65 Shore A. The first, second and third polymer tubing layers may each have thickness of 0.25-0.05 inches before lamination.

The metal helical coil layer 104 can be made of a metal such as stainless steel, titanium alloy or cobalt chromium and can be 0.005-0.020 inches thick.

The first and second braid layers 102, 107 may be made of a material such as Polyether ether Ketone (PEEK), steel alloy, or Nickel Titanium alloy, having a higher stiffness than the polymer tubing, and having a high yield strain (e.g., 4-10%).

As will be appreciated, providing multiple layers of braid embedded in an elastomeric matrix throughout the length of the flexible tubular member 11 can result in a flexible tubular member 11 that is resilient and sufficiently stiff and strong in the radial direction to resist collapse of the lumens, which must accommodate instruments and the endoscope 30. The resulting flexible tubular member 11 is also sufficiently flexible to bend and navigate through the tortuous path of a body lumen, while being sufficiently torsionally rigid that it can accommodate torque transmission, to thereby allow a user to torque the handle to rotate the adjustable cage 40 and orient the endoscope 30 and instruments to desired positions for accessing a lesion.

In some embodiments, the distal end 68 of the flexible tubular member 11 may couple to the cap member 75 adjacent to the adjustable cage 40, while the proximal end 90 of the flexible tubular member 11 may attach to the handle 24. The distal end 101 will have less torsional rigidity than the proximal end 103. Since the proximal end 103 of the flexible tubular member 11 does not have to be as flexible as the remainder of the flexible tubular member, additional reinforcement using a metal coil and thicker polymer matrix is provided to further increase torsional and radial stiffness/strength near the handle.

As shown in FIGS. 6-8, the proximal end 90 of the flexible tubular member 11 is coupled to the handle 24. The handle 24 includes four actuators 52, 54, 56, 58, each of which is coupled to a respective one of the plurality of flexible elements 42, 44, 46, 48. Each of the plurality of actuators 52, 54, 56, 58 can be slid back (i.e., away from the adjustable cage 40) to shorten the associated flexible element 42, 44, 46, 48 and place that member in tension, or can be slid forward (i.e., toward the adjustable cage 40) to lengthen the associated flexible element. As previously mentioned, the actuator 52, 54, 56, 58 can be locked in a desired position via interaction of a spring-loaded plunger and associated ratchet teeth associated with the handle 24. The user can release the lock by pressing the plunger and can slide the actuator in either direction (i.e., toward or away from the adjustable cage).

The flexible elements 42, 44, 46, 48 can be made from material having a stiffness and strength similar to metals such as Nickel Titanium, Cobalt Chromium or Stainless Steel. In some embodiments, the flexible elements 42, 44, 46, 48 can be constrained within respective braided tubes (e.g., metal braid in polyimide having a thickness of between 0.003-0.010") within the flexible tubular member 11. The braided tubes can each have an inner diameter 0.001-0.008 inches larger than the diameter of the associated flexible element 42, 44, 46, 48 to allow flexible elements to slide axially (i.e., along the longitudinal axis A-A of the system 10). The braided tubes may be attached to proximal and distal ends 90, 68 of the flexible tubular member 11 to maintain the flexible elements 42, 44, 46, 48 aligned and located about the circumference of the flexible tubular member. In some embodiments, the braided tubes are free floating inside the flexible tubular member 11 to enable the flexible tubular member to easily flex to navigate through tortuosity. In some embodiments, the braided tubes may be adhered to an inner surface of the flexible tubular member 11. In other embodiments, the braided tubes may be allowed to "float" within the flexible tubular member 11.

Figure 11:
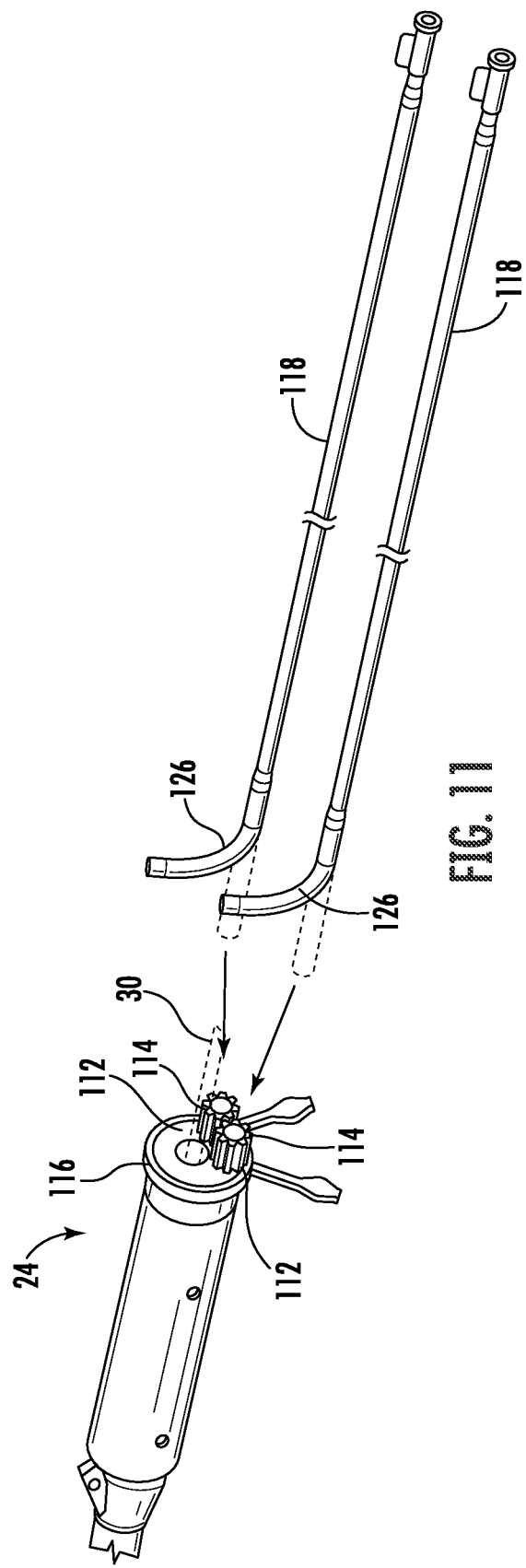
FIG. 11 is an isometric view of the handle portion of the system of FIG. 1, shown in the context of example instrument guides.

As shown in FIG. 11, the handle 24 may include one or more ports 112 with associated sealing valves 114 disposed at a proximal end 116 of the handle to allow for insertion of one or more instruments guides (and/or instruments) 118 and an endoscope 30. The lumens 12, 14, 28 may be in communication with such ports 112 so that the instrument guides 118, 128 and endoscope can be inserted through the proximal end 116 of the handle 24 and extended through the flexible tubular member 11 to access the working space 70 associated with the adjustable cage 40 (FIG. 2). Tubing (not shown) can be coupled to the ports 112 and can be disposed within the handle 24 to couple the ports 112 to the lumens 12, 14, 28 of the flexible tubular member 11. In some embodiments the tubing can be a flexible polymer such as fluoropolymer (Teflon) to guide the passage of instruments guides (and/or instruments) and the endoscope 30. As previously noted, the first and second lumens 12, 14 may likewise be made from fluoropolymer (Teflon) and may be allowed float freely inside the lumen 28 of the flexible tubular member 11 to enable the flexible tubular member to maintain a desired flexibility. The endoscope 30 may reside within the portion of the lumen 28 not taken up by the first and second lumens 12, 14. Thus, the effective lumen for the endoscope 30 is not round, but instead is formed by the convex outer diameters of the first and second lumens 12, 14, and the inner surface 15 of the flexible tubular member 11. This results in gaps between the endoscope 30 and the first and second lumens 12, 14 and inner surface 15 of the flexible tubular member, which reduces friction between the endoscope and those surfaces.

Figure 12:
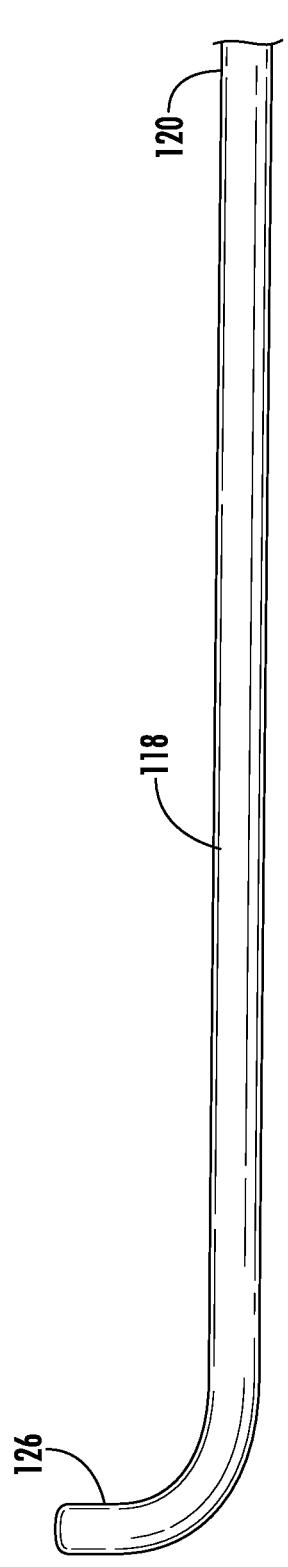
FIG. 12-14 are side views of example hockey stick and cobra instrument guides and a tissue manipulator for use with the system of FIG. 1.
Figure 15:
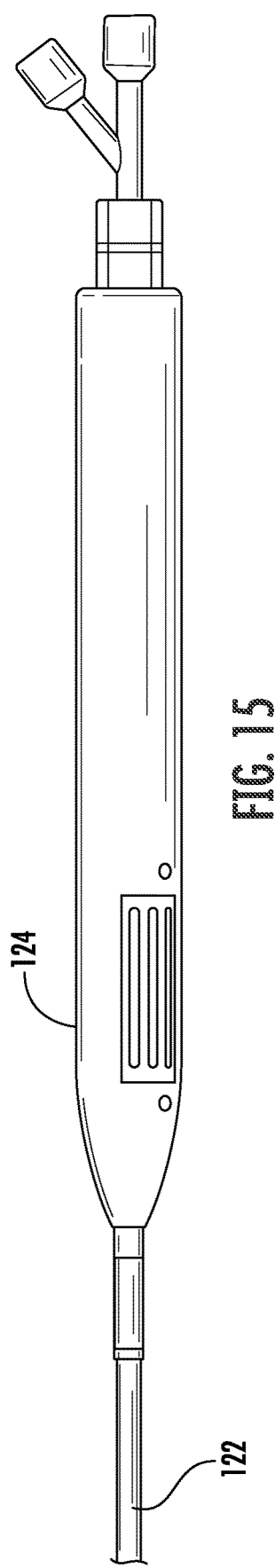
FIGS. 15 and 16 are side views of example instrument guide and tissue manipulator handles for use with the instrument guides and manipulator of FIGS. 12-14.

FIG. 12 shows an example first instrument guide 118 for insertion through one of the ports 112 and lumens 12, 14. The first instrument guide 118 has a proximal end 120 that can be coupled to a distal end 122 of handle member 124 (FIG. 15). The first instrument guide 118 may have a distal end 126 that, when extended through an associated lumen 12, 14 in the flexible tubular member 11, can position an instrument disposed therethrough to enable a user, by manipulating the handle member 124, to perform an operation within the working space 70 formed by the adjustable cage 40. The illustrated first instrument guide 118 has a single bend "hockey stick" arrangement at the distal end 126.

Figure 13:
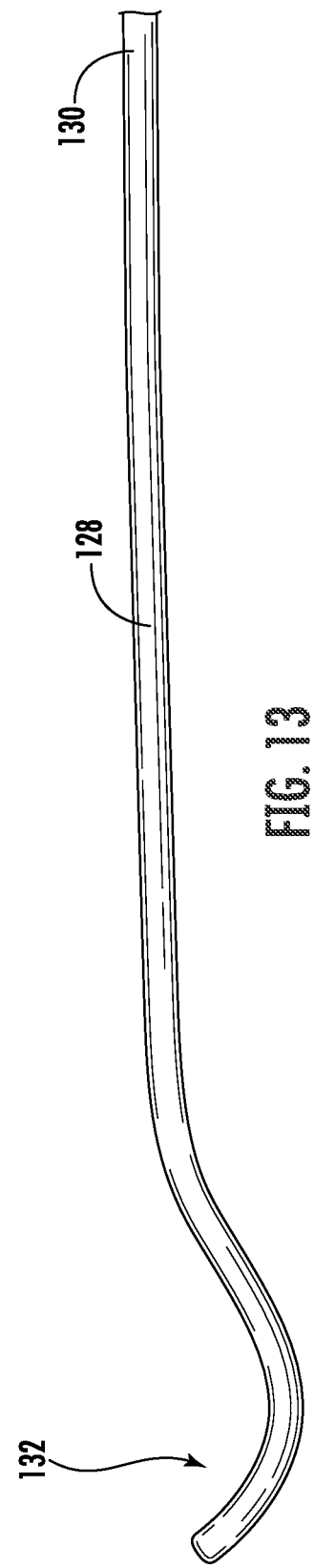

FIG. 13 shows an example second instrument guide 128 for insertion through one of the ports 112 and lumens 12, 14. The second instrument guide 128 has a proximal end 130 that can be coupled to the distal end 122 of the handle member 124 (FIG. 15). The second instrument guide 128 can have a distal end 132 that, when extended through an associated lumen 12, 14 in the flexible tubular member 11, can position an instrument disposed therethrough to enable a user, by manipulating the handle member 124, to perform an operation within the working space 70 formed by the adjustable cage 40. The illustrated second instrument guide 128 has a double bend "cobra" arrangement at the distal end 126.

The instrument guides 118, 128 may have a laminated braid construction, including high strain spine strips or wires (e.g., heat shaped nickel titanium or stiff polymer to curve) embedded at the distal ends 126, 132 to maintain a strong and resilient end portion. Proximal to the curved tip can be a rigid tube (e.g., metal) from 0.5-3.0 inches long to prevent that section from flexing when the instrument is used to lift a lesion. The distal ends 126, 132 can be deflectable to direct an instrument towards the target lesion or to position the distal ends farther away from lesion for better retraction.

Figure 14:
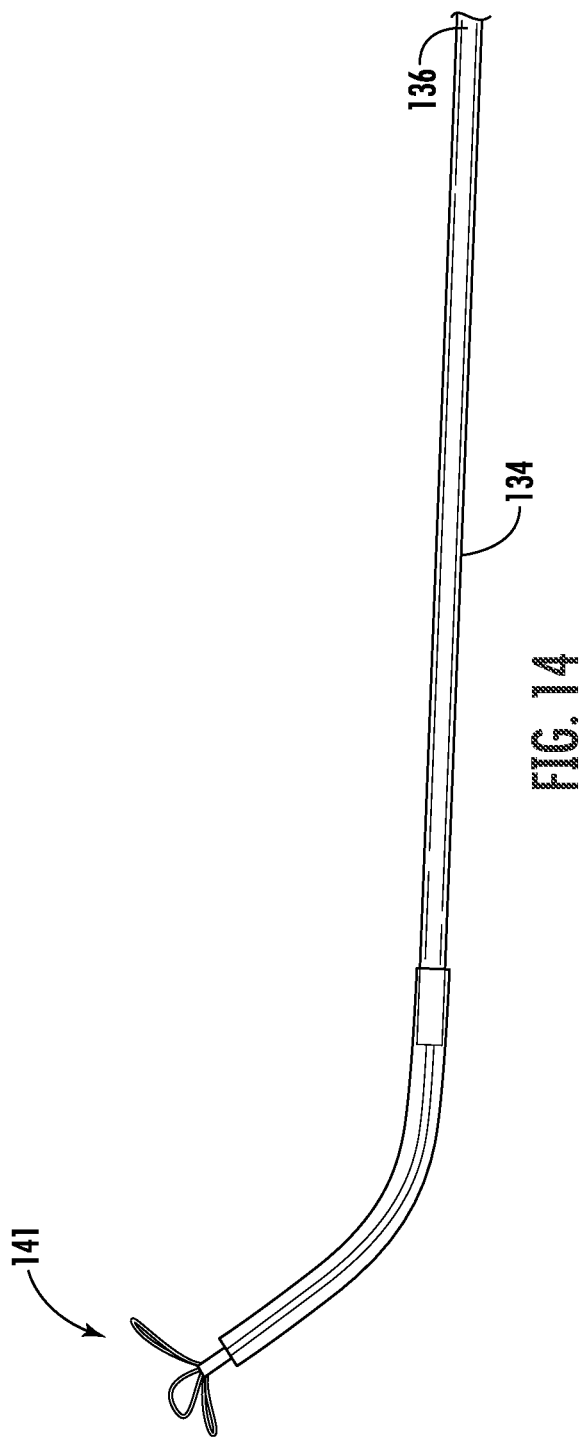
Figure 16:
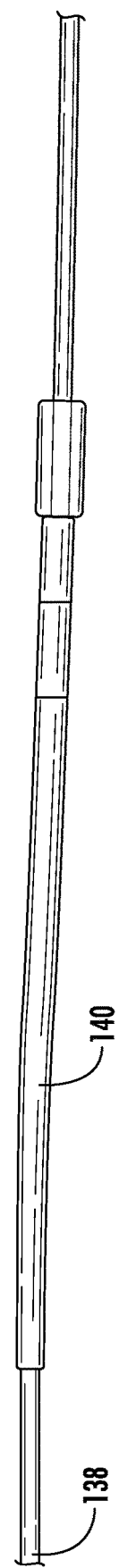

FIG. 14 shows an example tissue manipulator 134 for insertion through one of the ports 112 and lumens 12, 14. The tissue manipulator 134 has a proximal end 136 that can be coupled to a distal end 138 of the manipulator handle member 140 (FIG. 16). The tissue manipulator 134 can have a distal end 141 that, when extended through an associated lumen 12, 14 in the flexible tubular member 11, can enable a user manipulating the handle member 140 to engage and manipulate tissue within the working space 70 formed by the adjustable cage 40.

It will be appreciated that the first and second instrument guides 118, 128 and the tissue manipulator 134 are merely examples of structures that can be disposed through the ports 112 and lumens 12, 14 to perform operations within the working space 70 formed by the adjustable cage 40. Thus, a wide variety of tissue manipulators and instrument guides having shapes different from those described in relation to FIGS. 12-14 can be used without departing from the present disclosure. In addition, it will be appreciated that the system 10 can be used with "smart" instruments having self-articulating distal working ends (i.e., they do not require the use of instrument guides in order to engage tissue in the working space 70). One of ordinary skill in the art will understand that other types of instruments can also be inserted through the instrument guides 118, 128, a non-limiting example list of which includes ultrasound probes and any of a variety of diagnostic, imaging and other types of probes.

As, mentioned, during insertion into the body lumen and navigation to the lesion, the actuators 52, 54, 56, 58 can be moved together to retract all of the flexible elements 42, 44, 46, 48 to configure the adjustable cage 40 in the retracted configuration. This configuration can facilitate movement of the system around curves in the body lumen. As will be understood, curvatures in body lumens at or near targeted lesions can cause the adjustable cage 40, and thus the endoscope 30 and any instruments inserted through the lumens 12, 14, to be biased or wedged against the outside portion of the curve. To counter this, some or all of the flexible elements 42, 44, 46, 48 can be selectively adjusted to center the adjustable cage 40, and thus the instruments and endoscope 30 with respect to the lesion. For example, one or more of the flexible elements 42, 44, 46, 48 positioned adjacent to such an outside curvature in the body lumen can be tensioned while one or more of the remaining flexible elements can be retracted, thereby flexing the adjustable cage and reshaping the body lumen to center the adjustable cage and the instruments and instrument guides over the lesion. The flexible elements 42, 44, 46, 48 that are compressed can arch outward against the body lumen wall to create an operating and visualization space for working on the target lesion.

Figure 17:
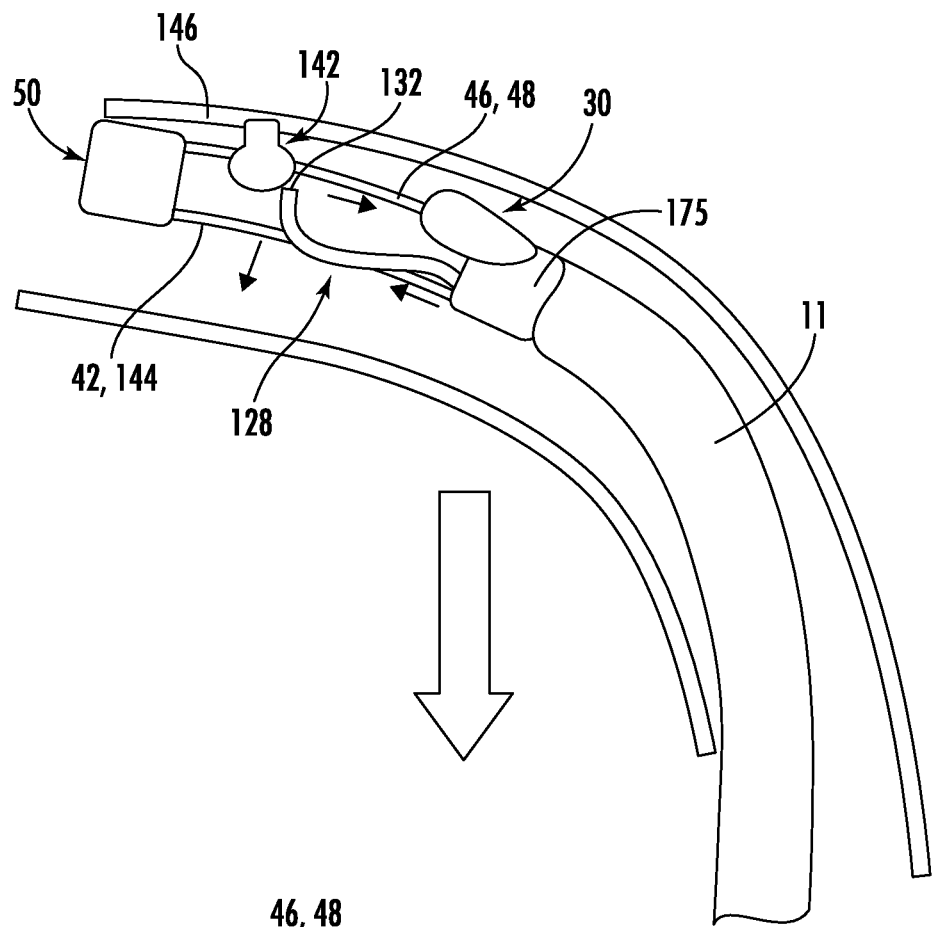
FIGS. 17-24 illustrate various positionings of the system of FIG. 1 to approach lesions in different locations with an example body lumen.
Figure 18:
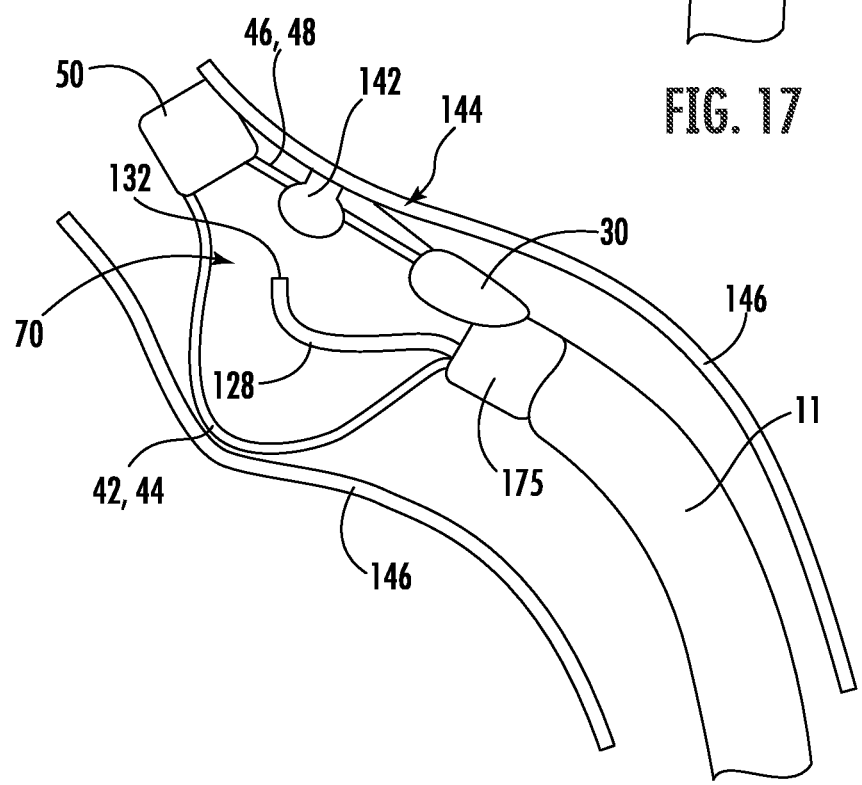

FIGS. 17-18 show an approach in which a lesion 142 is disposed on the outer curve of a body lumen 146. By expanding the adjustable cage 40 toward a side of the body lumen opposite that of the lesion 142, a larger working space 70 can be created for the instrument guide 128 to arch away from the lesion and rotate freely. Specifically, at least one of the flexible elements (e.g., flexible elements 42, 44) positioned on a side of the adjustable cage 40 facing away from the lesion 142 may be extended (by moving the associated actuators 52, 54 toward the adjustable cage 40), while the remaining flexible elements (e.g., flexible elements 46, 48) may be held stationary or may be retracted slightly (by maintaining the associated actuators 56, 58 stationary, or moving them slightly away from the adjustable cage 40). In addition to expanding the adjustable cage in a direction away from the lesion 142, this action can cause the cap member 50 to push the lesion 142 away from the distal end 132 of the second instrument guide 128. This can increase the working space 70 so that forceps (not shown) can extend from the second instrument guide 128 to grasp the lesion 142 and retract the lesion by pulling the forceps back into the second instrument guide. In the illustrated embodiment, a dissector 144 is extendable from the endoscope 30 to dissect or resect the lesion 142 for removal.

Figure 19:
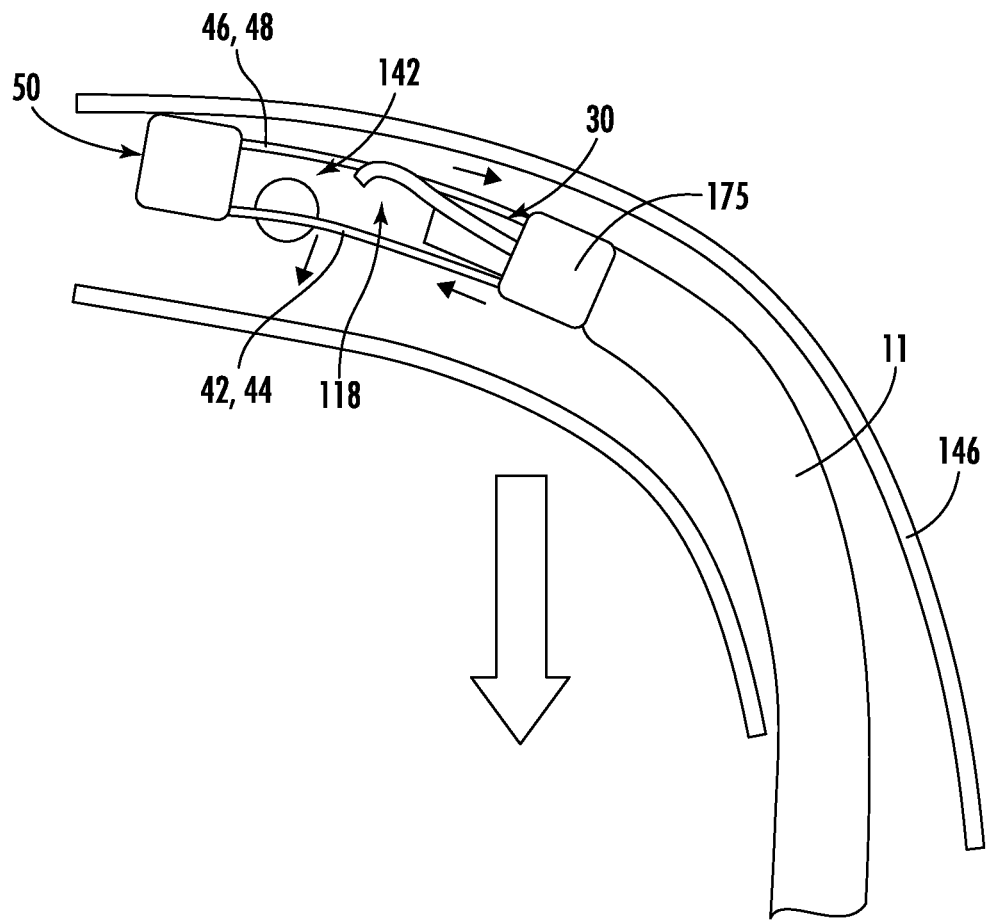
Figure 20:
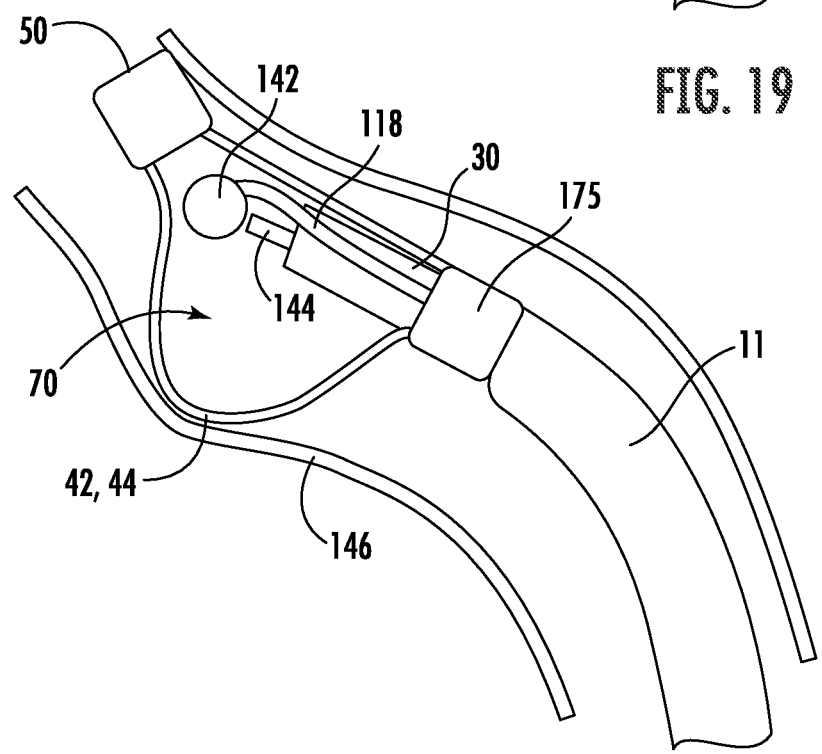

FIGS. 19-20 show an approach in which a lesion 142 is disposed between inner and outer curve sections of a body lumen 146. By expanding the adjustable cage 40 toward one side of the body lumen 146, additional transverse space can be created to center the lesion and the instrument guide 118. Specifically, at least one of the flexible elements (e.g., flexible elements 42, 44) positioned on a side of the adjustable cage 40 facing away from the outer curve be extended (by moving the associated actuators 52, 54 toward the adjustable cage 40), while the remaining flexible elements (e.g., flexible elements 46, 48) may be held stationary or may be retracted slightly (by maintaining the associated actuators 56, 58 stationary, or moving them slightly away from the adjustable cage 40). This can centralize the lesion within the working space 70 so that forceps can extend from the first instrument guide 118 to can grasp the lesion 142 and retract the lesion by pulling the forceps back into the first instrument guide. In the illustrated embodiment, a dissector 144 is extendable from the endoscope 30 to dissect or resect the lesion 142 for removal.

Figure 21:
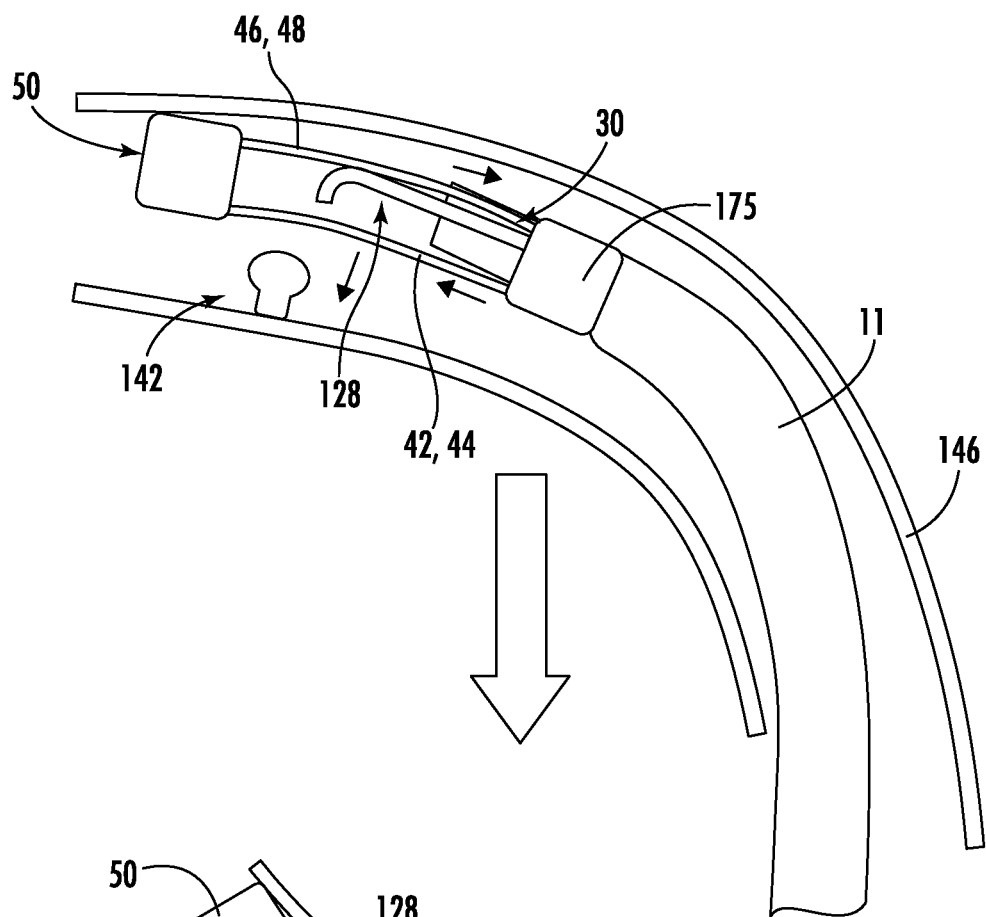
Figure 22:
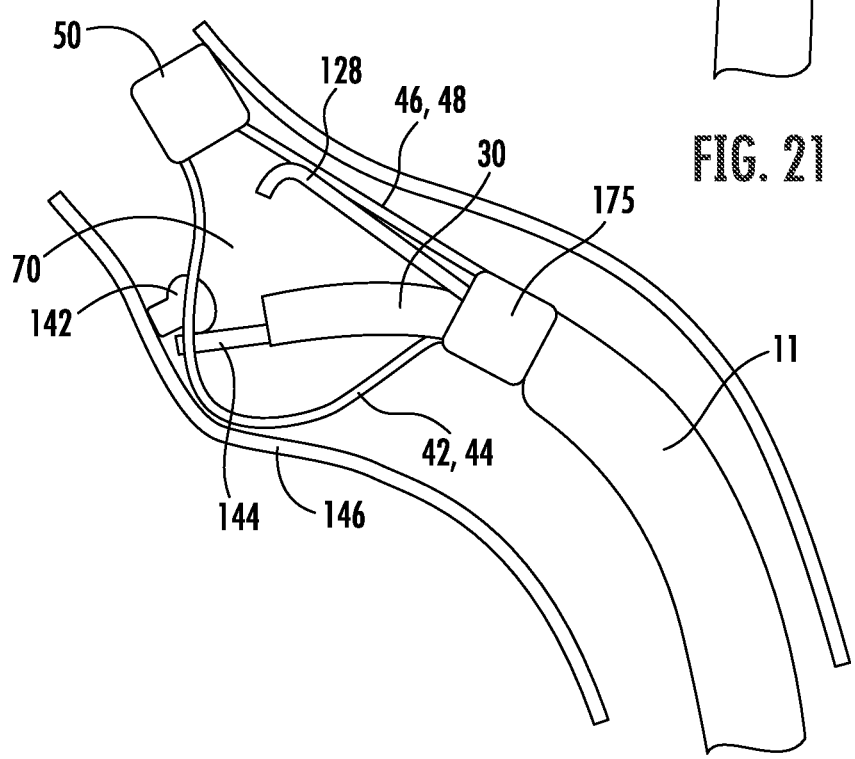

FIG. 21-22 show an approach in which a lesion 142 is disposed on an inner curve of a body lumen 146. In this case the first instrument guide 118 (i.e., the "hockey stick" shaped guide) is used to prevent the instrument guide from being wedged against the outer curve of the body lumen 146, which could otherwise limit movement of the instrument guide. The first instrument guide 118 is positioned a distance away from the lesion 142 so that it can direct a selected instrument directly at the lesion 142. Thus, at least one of the flexible elements (e.g., flexible elements 42, 44) positioned on a side of the adjustable cage 40 facing toward the lesion 142 can be extended (by moving the associated actuators 52, 54 toward the adjustable cage 40), while the remaining flexible elements (e.g., flexible elements 46, 48) may be held stationary or may be retracted slightly (by maintaining the associated actuators 56, 58 stationary, or moving them slightly away from the adjustable cage 40). In this position, an instrument can extend from the first instrument guide 118 to assist a dissector 144, which is extendable from the endoscope 30, to dissect or resect the lesion 142 for removal.

Figure 23:
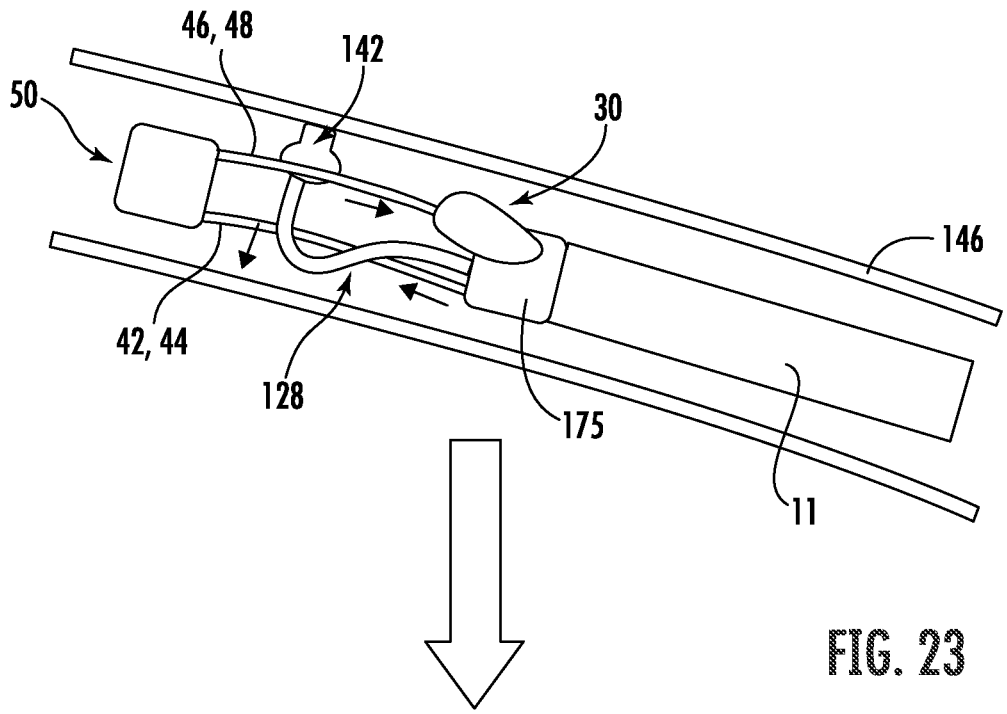
Figure 24:
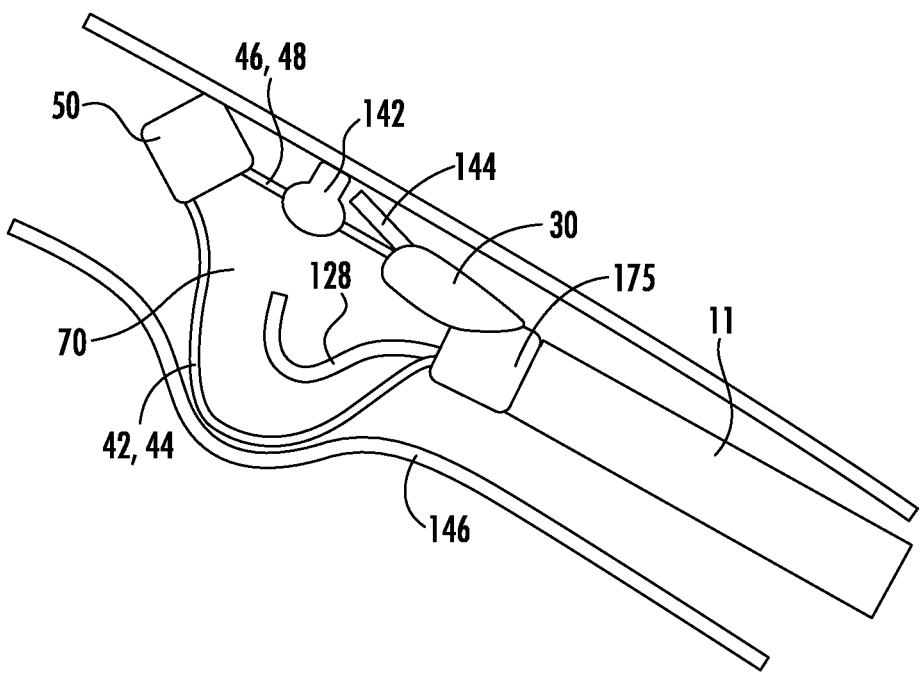

FIG. 23-24 show an approach in which a lesion 142 is disposed on a straight section of a body lumen 146. By expanding the adjustable cage 40 toward a side of the body lumen opposite that of the lesion 142, a larger working space 70 can be created for the instrument guide 128 to arch toward the lesion. Specifically, at least one of the flexible elements (e.g., flexible elements 42, 44) positioned on a side of the adjustable cage 40 facing away from the lesion 142 may be extended (by moving the associated actuators 52, 54 toward the adjustable cage 40), while the remaining flexible elements (e.g., flexible elements 46, 48) may be held stationary or may be retracted slightly (by maintaining the associated actuators 56, 58 stationary, or moving them slightly away from the adjustable cage 40). This can increase the working space 70 so that forceps (not shown) can extend from the second instrument guide 128 to grasp the lesion 142 and retract the lesion by pulling the forceps back into the second instrument guide. In the illustrated embodiment, a dissector 144 is extendable from the endoscope 30 to dissect or resect the lesion 142 for removal.

Table 1 provides guidance on the technique used for each scenario and appropriate Tool Guide shape. Shaping and orientation of the adjustable cage 40 involves correlating the orientation of the adjustable cage, instrument guides 118, 128 and endoscope 30 to the orientation of the handle 24 and actuators 52, 54, 56, 58. Therefore, the cap member 50 can have a unique color (i.e. magenta) on the endoscope 30 side (e.g., 12 o'clock) and the same color can be provided on the same side of the handle 24. Each flexible element 42, 44, 46, 48 can also have color markers visible through the endoscope 30. In some embodiments, the color markers re disposed on the distal ends of the flexible elements that corresponds with colors of the associated actuators 52, 54, 56, 58. By viewing the image from the endoscope 30, the user can determine which flexible element(s) 42, 44, 46, 48 to extend, and which flexible element(s) to retract, and can slide the appropriate actuator(s) either toward or away from the adjustable cage 40 accordingly.

TABLE 1

Guide to Cage Shaping and Tool Guide Shape Selection for Various Lesion Locations

| Lesion Location relative to lumen curvature | Cage Flexion | Tool Guide Shape Selection |
|---|---|---|
| Outer Section of lumen curvature | Towards outer curve | Cobra |
| Between Inner and Outer section of curvature | Towards outer curve | Cobra |
| Inner section of lumen curvature | Towards outer curve | Hockey Stick |
| On straight lumen | Towards lesion | Cobra |

A non-limiting example method for accessing a lesion 142 using the system 10 can begin with inserting an endoscope 30 through the flexible tubular member 11. The endoscope 30 may be extended through the opening 71 of the cap member 50 as far as possible. The adjustable cage 40 may be retracted to the second length (i.e., the retracted configuration) by moving all of the actuators 52, 54, 56, 58 way from the adjustable cage as far as possible. The endoscope can be inserted into the body lumen 146 and navigated to the site of interest (i.e., adjacent to a targeted lesion 142). The flexible tubular member 11 may then be inserted into the body lumen 146 and navigated to the site of interest until the adjustable cage 40 traverses the lesion 142 as seen through the visualization functionality of the endoscope 30. It will be appreciated that in some embodiments, the endoscope 30 and flexible tubular member 11 can navigate to the lesion site together, as a unit.

The handle 24 can be rotated to rotate the adjustable cage 40 so that the endoscope side of the adjustable cage straddles the lesion 142. The adjustable cage 40 can be configured in the extended position by moving all of the actuators 52, 54, 56, 58 toward the adjustable cage 40. The handle 24 may be used to position the cap member 50 just distal to the lesion 142. One or more of the actuators 52, 54, 56, 58 may be adjusted to position the cap in a desired orientation with respect to the lesion 142, and to expand the adjustable cage 40 in a manner that provides a desired working space 70 for the instrument guide(s) 118, 128 and the endoscope 30 to access the lesion 142. Table 1 may be used as a guide for shaping of the adjustable cage 40 and for instrument guide shape selection for various lesion locations.

If there is a fold in the body lumen 146 in front of lesion 142, the fold can be grasped using forceps (not shown) inserted through the first instrument guide 118, and the forceps may be used to push the fold down to expose the lesion 142. If there is a fold in the body lumen 146 behind the lesion 142, the fold can be grasped using forceps and the forceps may be retracted into the instrument guide 118. The instrument guide 118 may then be pushed forward to expose the lesion 142 for resection. An injection needle (not shown) can be inserted through an instrument channel of the endoscope and dye can be injected into the lesion 142.

An appropriate instrument guide 118, 128 can be selected based on the criteria of Table 1. A grasper (not shown) can be inserted through the selected instrument guide 118, 128 and the two can be inserted through a selected port 112 in the flexible tubular member 11. The lesion 142 can be grasped using the grasper, and the grasper may be retracted until the jaws of the grasper retract inside the distal end of the instrument guide. Alternatively, the grasper can be extended away from the connected lesion to facilitate subsequent dissection. The instrument guide 118, 128 may be twisted to increase retraction (i.e., lift) as needed.

A dissector (e.g., dual knife, scissor, or the like) may be extended through a lumen 12, 14 in the endoscope 30. The endoscope 30 may be positioned near the lesion 142, and the dissector 144 may be advanced to engage the lesion 142. The endoscope 30 may be used to steer the dissector to the lesion 142, and the lesion may be separated from the body lumen 146 using the dissector. The grasper along with the instrument guide can then be retracted into its respective lumen to remove the lesion 142.

FIGS. 25-33 illustrate an embodiment of a system 200 for performing minimally invasive procedures in a body lumen. The system 200 may include a flexible tubular member 211 having some or all of the features (e.g., insufflation port(s), lumen(s) for receiving instrument guides and instruments, endoscopes, and the like, construction to facilitate torque transmission, and the like) described in relation to the flexible tubular member 11 of FIGS. 1-24. The flexible tubular member 211 may also include a handle (not shown) having some or all of the features described in relation to the handle 24 of FIGS. 1-24, including a plurality of actuators similar to the actuators 52, 54, 56, 58 described in relation to FIGS. 1-24. An adjustable cage 240 may be disposed at a distal end 213 of the system 200 for positioning within the body lumen adjacent a targeted lesion.

As will be discussed, the system 200 is configured to enable a user to access a targeted lesion within a body lumen, and to perform one or more operations on the lesion using any of a variety of instruments disposed through lumens in the flexible tubular member 211 and/or an endoscope 230 disposed through the flexible tubular member 211. The adjustable cage 240 may include a plurality of flexible elements 242, 244, 246, 248, each of which can be independently movable by an associated actuator disposed in or on the handle. As with the prior embodiment, independent adjustment of each of the plurality of flexible elements 242, 244, 246, 248 can result in a desired change in shape of the adjustable cage 240.

The adjustable cage 240 of the present embodiment may be used to control the position and orientation of a cap member 250 disposed at a distal end thereof. As will be discussed, a plurality of instruments and/or instrument guides 218, 228 may protrude through the cap member 250 to perform one or more operations disposed beyond the cap member. Thus, in contrast to the prior embodiment, the adjustable cage 240 may not itself form a working space within which an operation on the lesion will be formed. Instead, the adjustable cage 240 may function as a steering unit to steer the plurality of instruments and/or instrument guides 218, 228 toward a lesion disposed beyond the adjustable cage and the cap member 250.

The adjustable cage 240, in combination with the handle, may also be used to press the cap member 250 against the lesion and/or tissue adjacent to the lesion, in order to provide the instruments inserted therethrough to perform one or more operations on the lesion.

The adjustable cage 240 may include first and second working channels 252, 254 coupled between the first and second lumens 212, 214 of the flexible tubular member 211 and the cap member 250. One or more instruments and/or instrument guides 218, 228, inserted through the first and second lumens 212, 214, can be disposed through the first and second working channels 252, 254 to protrude from a distal end 256 of the cap member 250. In one non-limiting example embodiment, the first and second working channels 252, 254 comprise flexible polymer tubing that is adhered or otherwise fixed to an inner surface of the cap member 250. Distal ends (not shown) of the first and second working channels 252, 254 may be oriented so that instruments and/or instrument guides disposed therethrough can exit the distal end 256 of the cap member 250 through one or more of the slits 258 formed in the cap member.

Although the illustrated embodiment shows two working channels, it is contemplated that greater or fewer working channels can be used. As will be appreciated, the first and second working channels 252, 254 may eliminate the need for instrument guides, because the working channels themselves may act as instrument guides, orienting the instruments in a desired manner through adjustment of the position of the cap member 250.

Thus, the system 200 contemplates that a working space is formed distal to the cap member 250, and that the cap member 250 controls the position and orientation of the instruments inserted through the working channels 252, 254.

For embodiments that do not employ instrument guides, a variety of "smart" instruments (i.e., instruments that include their own articulation functionality) can be used, including graspers, knives, retractors and the like. Traditional instruments can also be used, with or without instrument guides as desired.

The adjustable cage 240 may also include a connection member 270 coupled between the cap 275 disposed on the distal end 268 of the flexible tubular member 211 and the cap member 250. In one non-limiting example embodiment, the connection member 270 is a flexible metallic braided tube that provides a desired offset between the distal end 268 of the flexible tubular member 211 and the cap member 250. The connection member 270 acts as a "spine" for the adjustable cage 240, to minimize stress placed on the working channels 252, 254 during system placement, orientation, and operation. In some embodiments, the connection member 270 may also include a flexible polymer tube 274 (see FIGS. 27, 31, 32) surrounding the flexible metallic braided tube.

Figure 25:
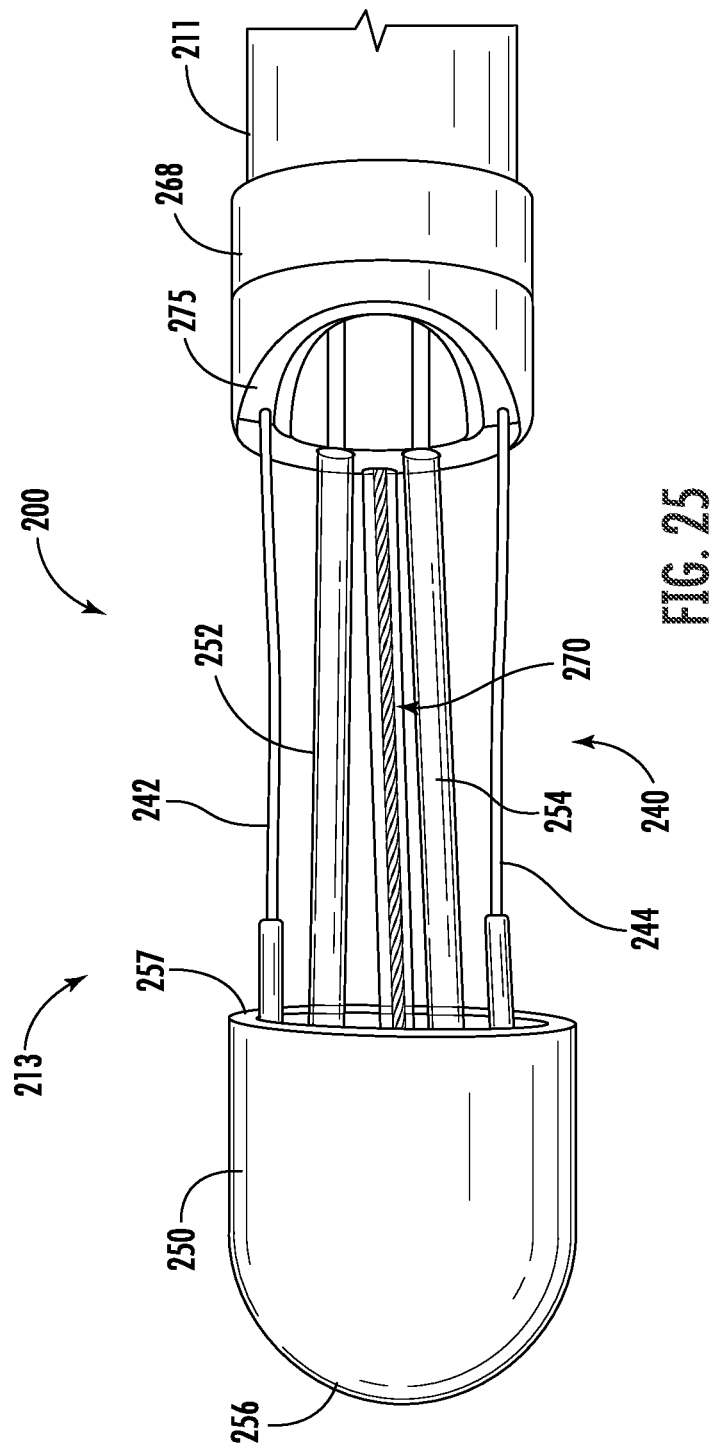
FIG. 25 is a top view of an adjustable cage of the system of FIG. 1 according to the present disclosure.
Figure 26:
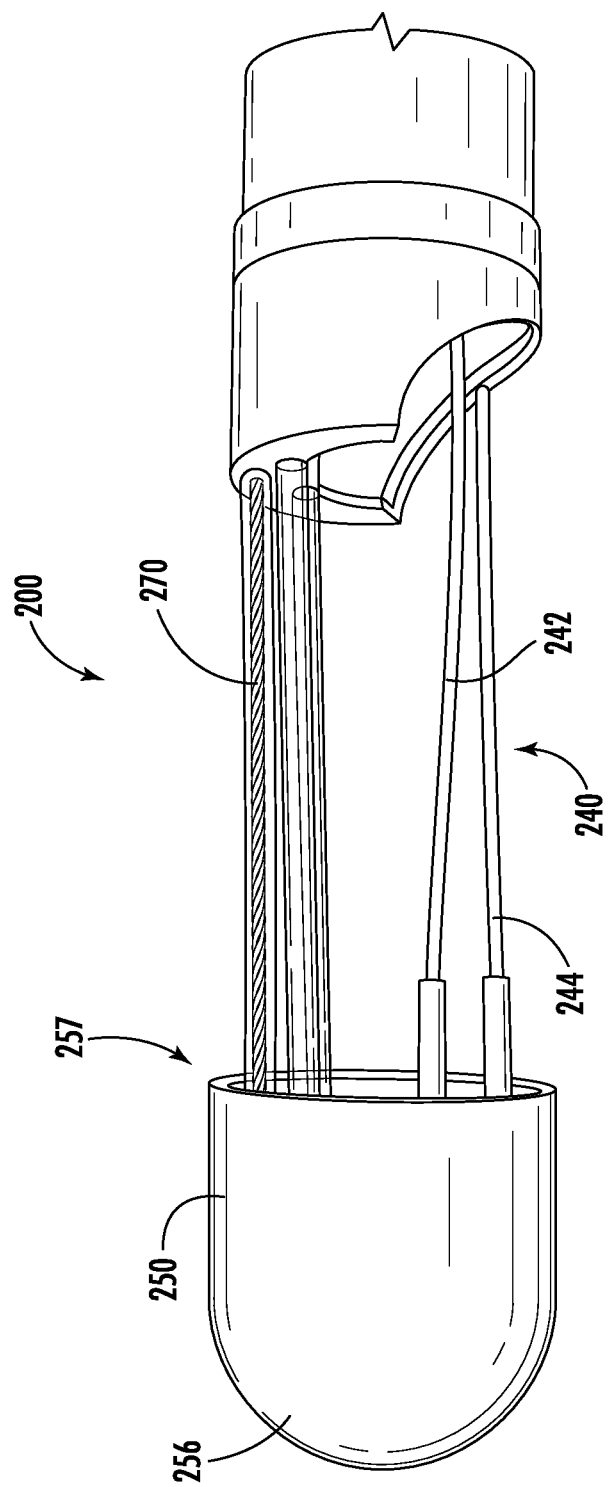
FIG. 26 is a side view of the adjustable cage of FIG. 25
Figure 27:
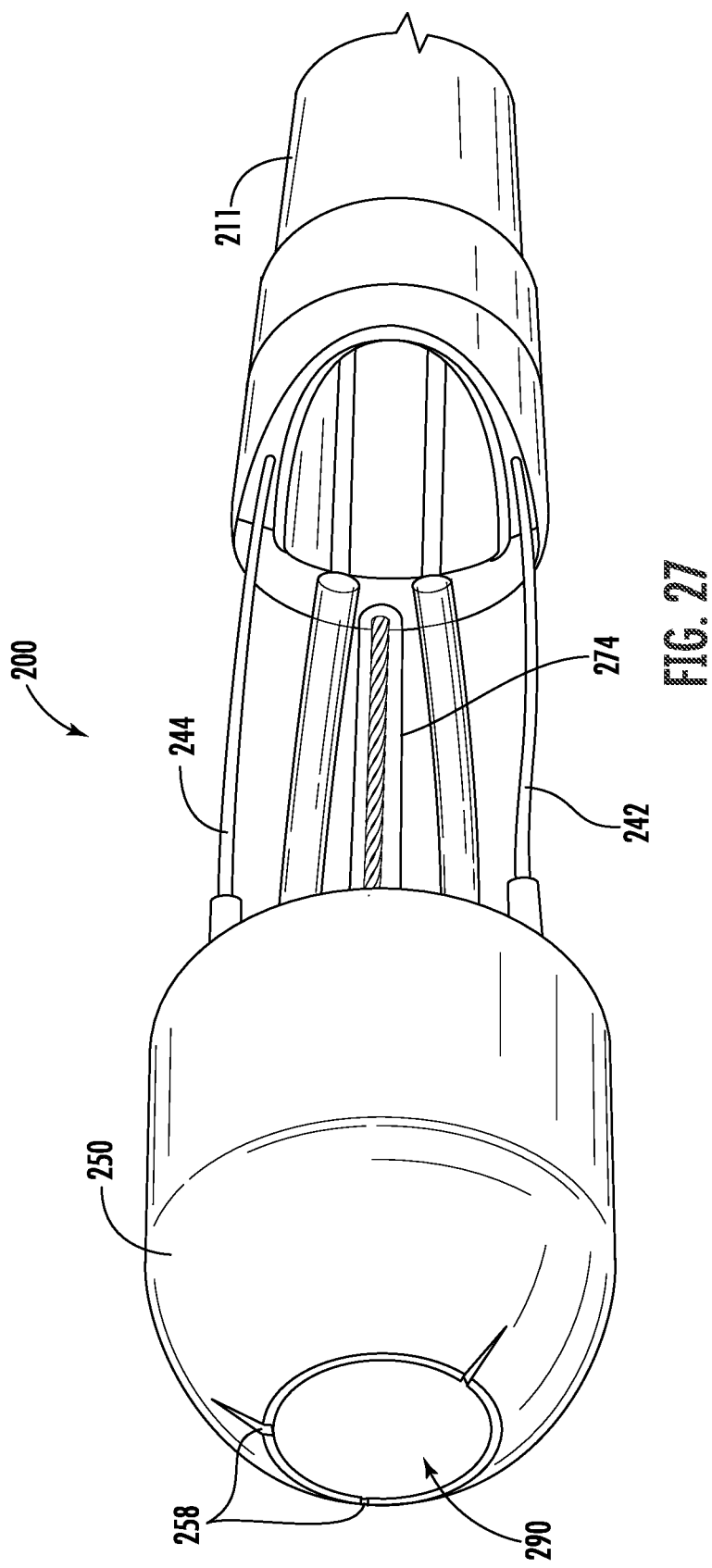
FIG. 27 is an isometric view of the adjustable cage of FIG. 25.

FIG. 25 shows the adjustable cage 240 is shown in a collapsed configuration. As will be appreciated, the adjustable cage 240 may be positioned in this collapsed configuration when the flexible tubular member 211 is inserted into the body lumen. Once the adjustable cage 240 is navigated through the body lumen and positioned adjacent to a targeted lesion, the user may selectively expand the adjustable cage into an expanded configuration which, as will be described in greater detail later, can position a cap member 250 coupled thereto in a desired orientation and to orient one or more instruments and/or instrument guides 218, 228 with respect to a targeted lesion.

Figure 31:
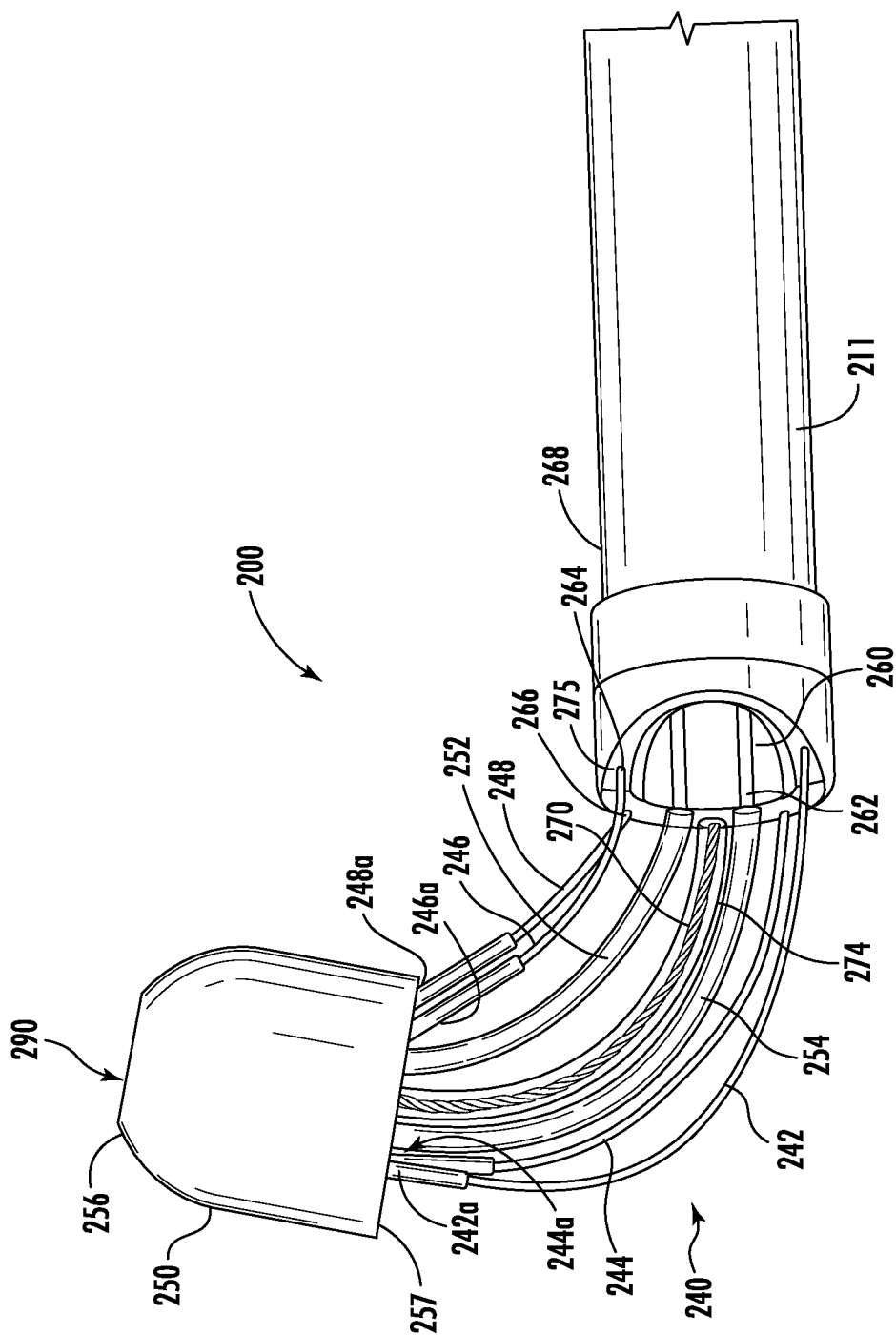
FIG. 31 is a side view of the adjustable cage of FIG. 25 with the cap of the adjustable cage in an alternate laterally angled position.
Figure 32:
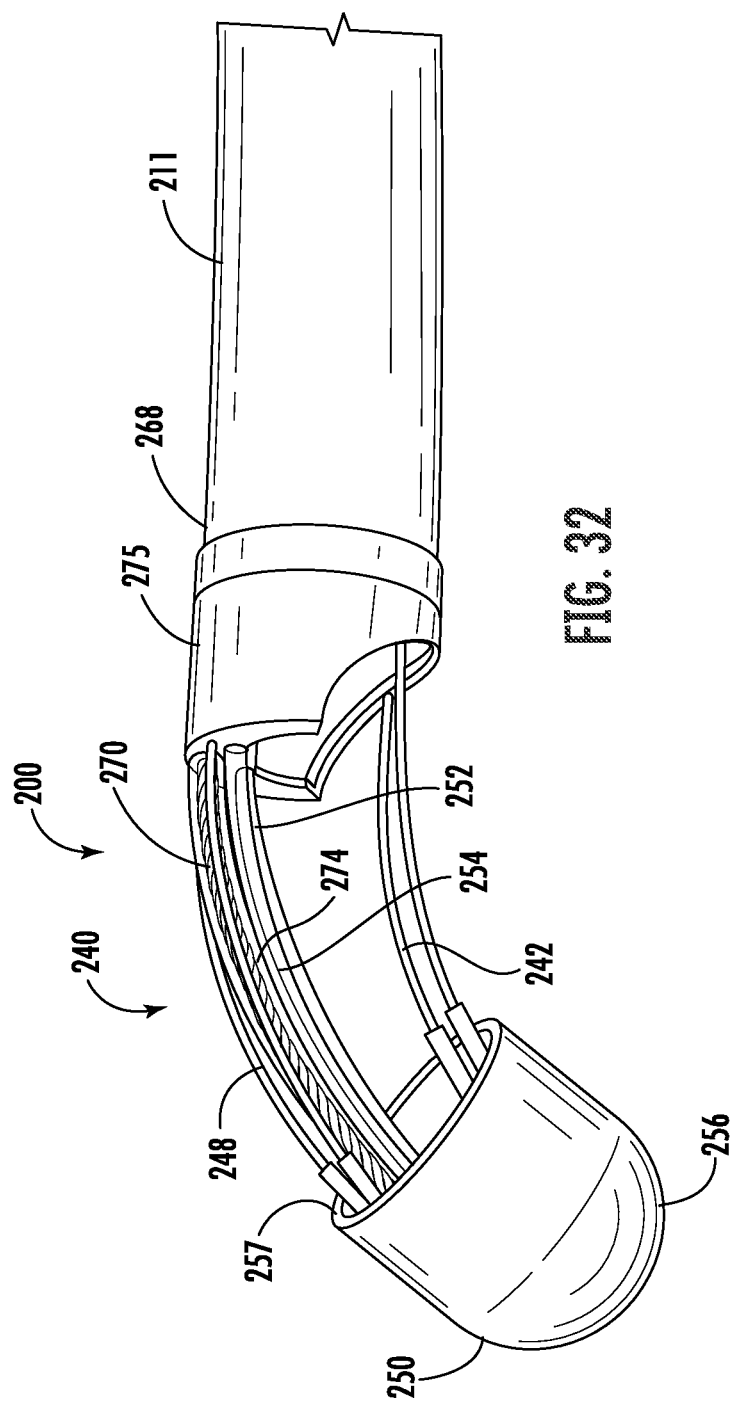
FIG. 32 is a side view of the adjustable cage of FIG. 25 with the cap of the adjustable cage in a further alternate laterally angled position.
Figure 33:
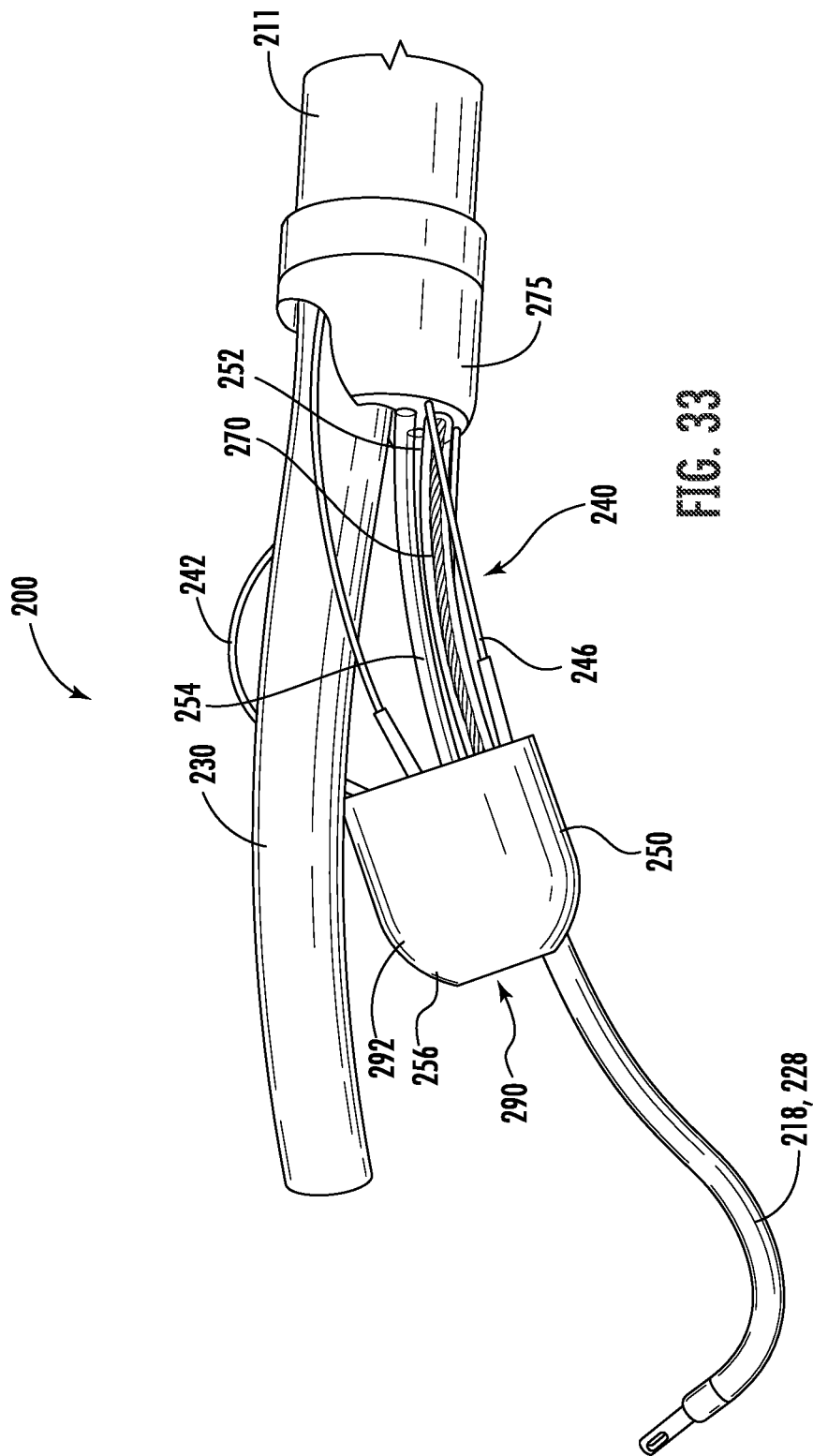
FIG. 33 is a side view of the adjustable cage of FIG. 25 with an endoscope and an instrument guide in extended positions with respect to the adjustable cage.

As shown most clearly in FIG. 31, the adjustable cage 240 may comprise a plurality of flexible elements 242, 244, 246, 248, that can be independently adjustable to enable a user to selectively adjust a size and shape of the adjustable cage. In the illustrated embodiment, the plurality of members 242, 244, 246, 248 comprise a plurality of wires that form a cage. It will be appreciated that although the illustrated embodiment includes four flexible elements, greater or fewer flexible elements can be employed to form the adjustable cage 240. In addition, although the illustrated embodiment shows the flexible elements as being wires, the flexible elements can be made from any structural elements that can provide the desired functionality as will be described herein.

As shown, the plurality of flexible elements 242, 244, 246, 248 each have a distal end 242a, 244a, 246a, 248a that is fixedly coupled to the cap member 250. Proximal ends (not shown) of the plurality of flexible elements 242, 244, 246, 248 are coupled to respective actuators associated with the handle The flexible elements 242, 244, 246, 248 are received within longitudinal openings in the flexible tubular member 211 and exit through openings 260, 262, 264, 266 adjacent a distal end 268 of the flexible tubular member 211. The plurality of flexible elements 242, 244, 246, 248 can be independently extended and retracted with respect to the distal end 268 of the flexible tubular member 211 by individually actuating the respective actuators of the handle 24. In this manner, the shape of the adjustable cage 240 can be adjusted to adjust the position and orientation of the cap member 250 so that instruments inserted through the flexible tubular member 211 and the cap member can access a targeted lesion, as will be described in greater detail later.

Figure 28:
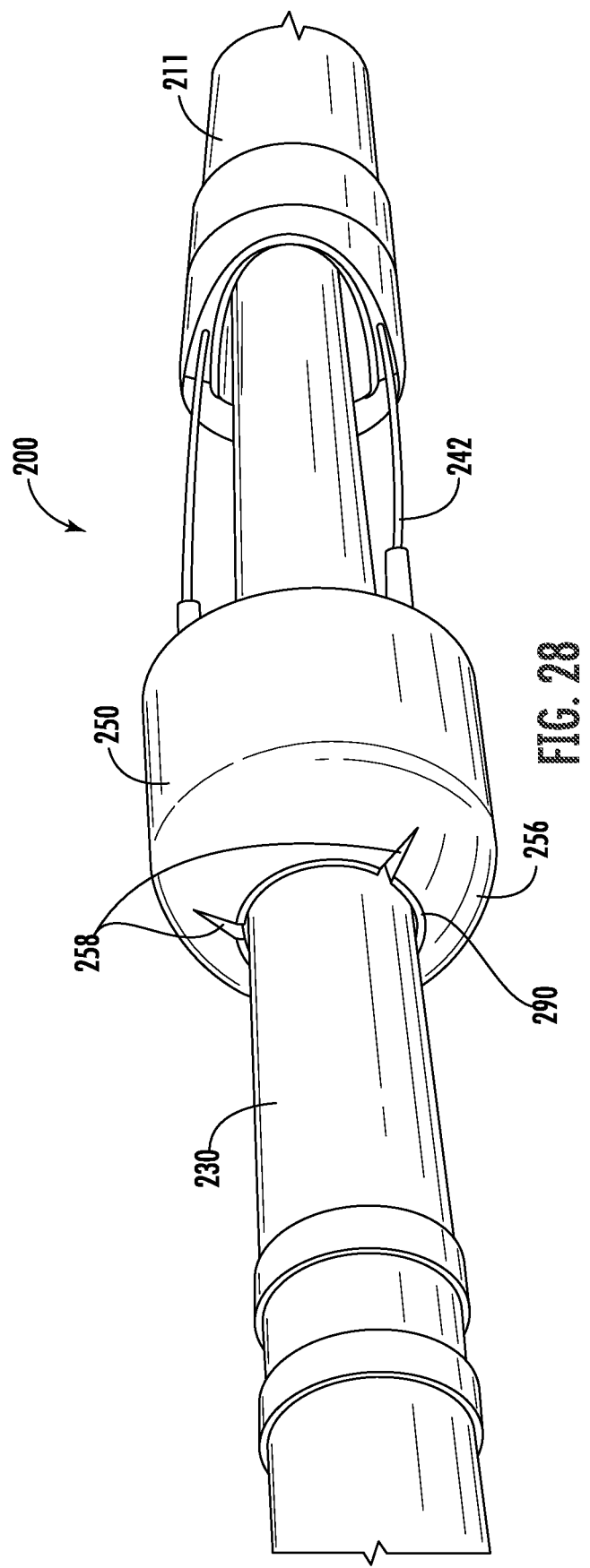
FIG. 28 is a further isometric view of the adjustable cage of FIG. 25 with an endoscope in an extended position.

As noted, the cap member 250 may have a generally cylindrical proximal end 257 coupled to the distal ends 242a, 244a, 246a, 248a of the plurality of flexible elements 242, 244, 246, 248. A connection member 270, including a flexible polymer tube 274 may also be coupled between the distal end 268 of the flexible tubular member 211, as will be discussed in greater detail later. The distal end 256 of the cap member 250 may have a curved shape configured to facilitating movement of the system 200 through the body lumen. The distal end 256 of the cap member 250 may have an opening 290 (FIG. 27) therethrough sized and shaped to receive the endoscope 230 therethrough. The opening 290 may include a plurality of slits 258 that radiate away from the opening. The slits 258 may allow the opening 290 to flex outwardly to accept the endoscope 230 therethrough, ensuring a snug fit between the cap member 250 and the endoscope to prevent tissue from being pinched between the cap member and the endoscope as the endoscope is moved through the opening. FIG. 28 shows the endoscope 230 extended through the opening 290.

Figure 29:
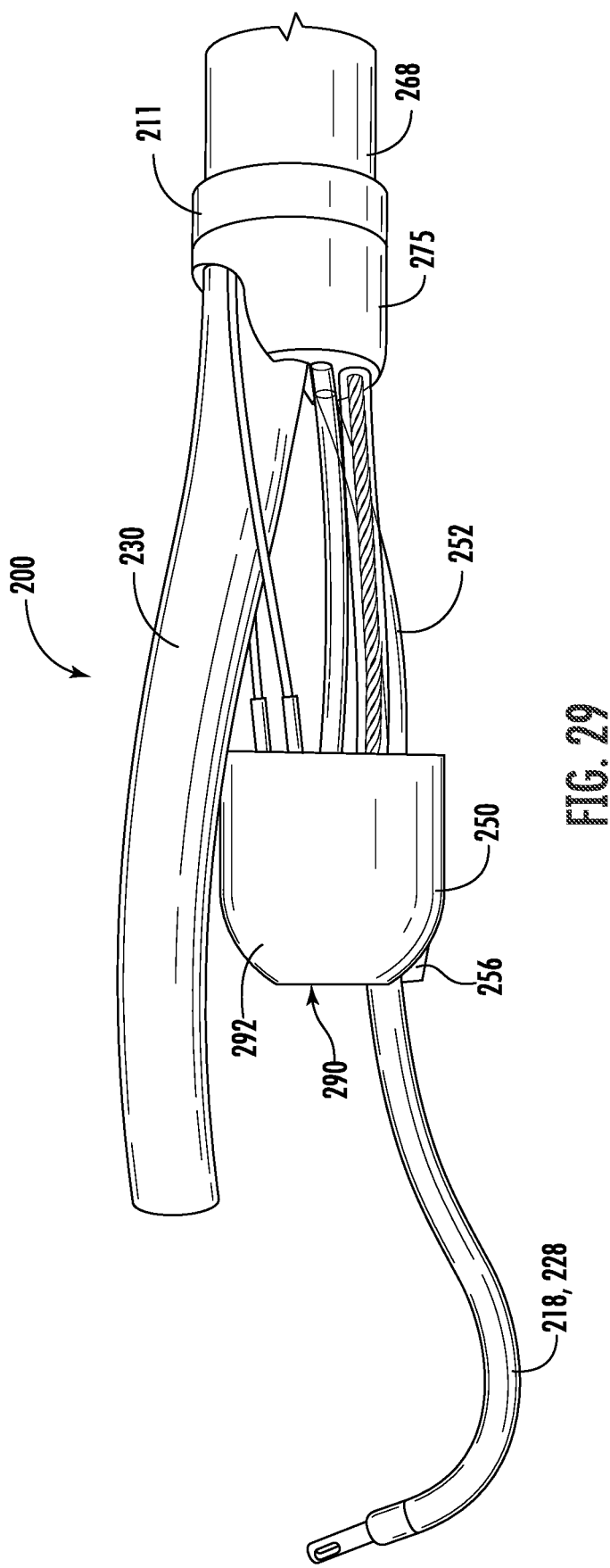
FIG. 29 is a side view of the adjustable cage of FIG. 25 with an endoscope and an instrument guide in extended positions with respect to the adjustable cage.

The cap member 250 may also have a side slit 292 that extends between the proximal and distal ends 257, 256 of the cap member. The side slit 292 may allow the endoscope to disengage through the side of the cap member 250 before, during, or after a procedure to allow the user freedom to move the endoscope to a desired position and orientation with respect to a targeted lesion. FIG. 29 shows the endoscope 230 laterally detached from the cap member 250. For example, in some embodiments the endoscope 230 may be positioned in or through the cap member 250 during navigation to the lesion and may then be moved outward through the side slit 292 to facilitate resection of the lesion.

Figure 30:
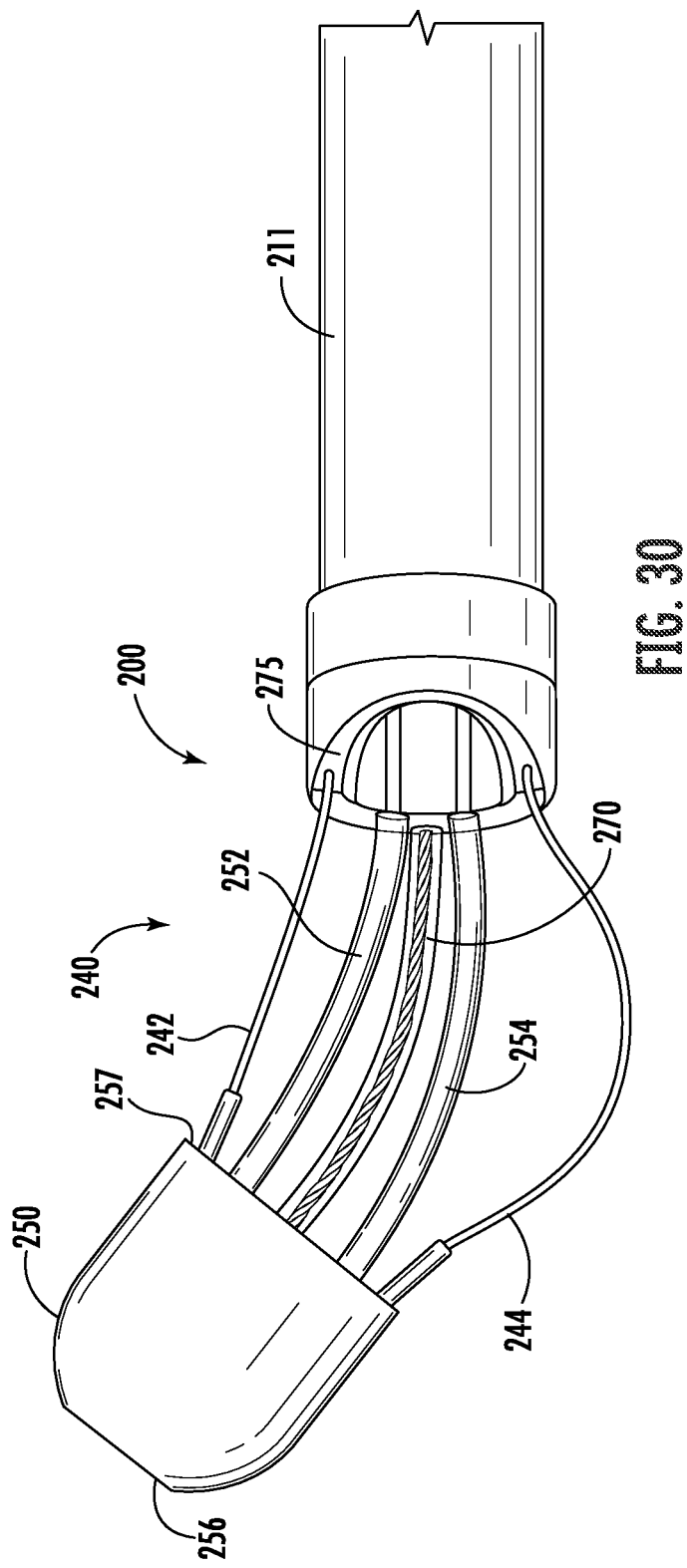
FIG. 30 is a top view of the adjustable cage of FIG. 25 with a cap of the adjustable cage in a laterally angled position.

FIG. 30 shows the adjustable cage 240 in an expanded configuration. In the illustrated configuration one of the flexible elements 244 is extended while the other flexible elements 242, 246, 248 are either maintained in place or retracted. This results in the adjustable cage being bowed on one side to provide a desired orientation of the cap member 250. Since the plurality of flexible elements 242, 244, 246, 248 are independently extendable/retractable, the adjustable cage 240 is infinitely adjustable by the user to provide a desired orientation of the cap member 250 depending on the shape of the body lumen and the position of the targeted lesion. This provides the user with an enhanced array of options for accessing a lesion using one or more instruments and an endoscope 30 disposed through the flexible tubular member 211.

As can be seen in FIG. 28, endoscope 230 is extendible through the adjustable cage 240 and also through the opening 290 in the cap member 50. As shown in FIG. 30, first and second working channels 252, 254 are also extendable through the adjustable cage 240 and the opening 290 in the cap member 250. The first and second working channels 252, 254 can receive first and second instrument guides 218, 228 which can receive first and second instrument therethrough. As will be appreciated, the disclosed arrangement can enable a variety of visualization and tissue manipulation functions to be performed on a targeted lesion disposed adjacent to the cap member 250.

A cap 275 may be disposed on or over the distal end 268 of the flexible tubular member 211. As shown in FIG. 31, the plurality of flexible elements 242, 244, 246, 248 are received through respective openings 276, 278, 280, 282 in the cap 275. The cap 275 can also include an opening 284 for receiving the endoscope 230 therethrough, and respective openings 286, 288 aligned with the first and second lumens 212, 214 in the flexible tubular member 211.

As previously noted, the system 200 can include a handle having actuators that are configured and have the same functionality to individually actuate the plurality of flexible elements 242, 244, 246, 248 as described in relation to FIGS. 1-25. As discussed, by enabling the individual flexible elements 242, 244, 246, 248 to be extended, retracted, or held in place via selective activation of one or more of the actuators, the adjustable cage 240 can be lengthened (i.e., extended), shortened (i.e., retracted), and/or otherwise adjusted to achieve a variety of configurations appropriate for positioning the cap member 250 in a desired orientation.

During insertion of the system 200 into the body lumen, and while navigating the adjustable cage 240 to a target lesion, the actuators on the handle can be allowed to "ride free" with respect to the handle to allow the plurality of flexible elements 242, 244, 246, 248 to naturally flex as the system passes the curves of the body lumen. In some embodiments, the distal tip of the endoscope may be slightly offset (e.g., ½ centimeter) from the cap member 250 during navigation of the body lumen in order to provide a degree of flexibility between the two. In some embodiments, the cap member 250 can be manipulated as it is moved through the body lumen in order to make it easier to pass the natural curves of the lumen.

Once the adjustable cage 240 has been navigated within the body lumen to a desired position with respect to the targeted lesion, the actuators can be adjusted to adjust the shape of the adjustable cage 240 to orient the cap member 250 toward the lesion.

The flexible elements 242, 244, 246, 248 can be made from the same or similar materials as those described in relation to the flexible elements of FIGS. 1-24. In addition, the flexible elements 242, 244, 246, 248 can be constrained within respective braided tubes within the flexible tubular member 211 in the same manner as described in relation to FIGS. 1-24.

A variety of instrument guides, instruments, and tissue manipulators, similar to those described in relation to FIGS. 1-24 can be used with the system 200.

A non-limiting example method for accessing a lesion using the system 200 may begin with inserting an endoscope 230 through the flexible tubular member 211. The endoscope 230 may be extended through the opening 290 of the cap member 250 as far as possible. The endoscope can be inserted into the body lumen and navigated to the site of interest (i.e., adjacent to a targeted lesion). The flexible tubular member 211 may then be inserted into the body lumen and navigated to the site of interest until the cap member 250 is positioned adjacent the lesion as seen through the visualization functionality of the endoscope 230. In some embodiments, the flexible tubular member 211 covers the endoscope 230 (up to the cap member 250) during navigation.

The handle can be rotated to rotate the adjustable cage 240 so that the endoscope side of the adjustable cage straddles the lesion. The handle may be used to adjust the position of the cap member 250 adjacent to the lesion. One or more of the actuators may be adjusted to expand the adjustable cage 240 in a manner that provides a desired position of the cap member 250 with respect to the lesion. If there are folds in front of or behind the lesion, forceps disposed through one of the working channels 252, 254 can be used to expose the lesion in the manners described.

The appropriate instrument guide 218, 228 can be selected. A grasper (not shown) can be inserted through the selected instrument guide 218, 228 and the two can be inserted through a selected lumen 212, 214 in the flexible tubular member 211. The lesion can be grasped using the grasper, and the grasper may be retracted until the jaws of the grasper retract inside the distal end of the instrument guide. The instrument guide 218, 228 may be twisted to increase retraction (i.e., lift) as needed.

A dissector (e.g., dual knife, scissor, or the like) may be extended through a lumen in the endoscope 230. The endoscope 230 may be positioned near the lesion, and the dissector may be advanced to engage the lesion. The endoscope 230 may be used to steer the dissector to the lesion, and the lesion may be separated from the body lumen using the dissector. The grasper and instrument guide may be retracted into the associated lumen 212, 214 in the flexible tubular member 211 to remove the lesion.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A system for performing minimally invasive procedures in a body lumen of a patient, the system comprising:
   a flexible tubular member having a first lumen for receiving an endoscope;
   an adjustable cage disposed at a distal end of the flexible tubular member, the adjustable cage comprising a plurality of flexible elements that are independently and selectively movable laterally outwardly to move a side wall of the body lumen outwardly to increase visualization and a working space within the body lumen;
   a handle having a plurality of actuators movably disposed with respect to a body portion of the handle, each of the plurality of actuators coupled to a selected one of the plurality of flexible elements such that moving one of the plurality of actuators extends or retracts the coupled flexible element to adjust a shape of the adjustable cage; and
   a cap member coupled to distal ends of the flexible elements,
   wherein the shape of the adjustable cage is selectively adjustable by actuating one or more of the plurality of actuators to orient the cap member towards a targeted lesion, and
   wherein the cap member comprises a lateral slit between proximal and distal ends of the cap member for allowing the endoscope to laterally disengage from the cap member through the lateral slit.

2. The system of claim 1, wherein the plurality of flexible elements are fixedly coupled between the plurality of actuators and a cap member disposed at a distal end of the system.

3. The system of claim 1, wherein the plurality of flexible elements comprise first, second, third and fourth flexible elements.

4. The system of claim 1, wherein the plurality of flexible elements comprise wires.

5. The system of claim 1, wherein the adjustable cage forms a working space therein.

6. The system of claim 1, wherein the cap member comprises an opening sized and configured to receive an endoscope therethrough.

7. The system of claim 6, wherein the cap member comprises one or more slits radiating from the opening.

8. The system of claim 1, further comprising a connecting member disposed between a distal end of the flexible tubular member and a proximal end of the cap member, the connecting member including a flexible braid element.

9. The system of claim 1, further comprising first and second working channels coupled between first and second lumens of the flexible tubular member and the cap member.

10. The system of claim 1, wherein the adjustable cage has a retracted configuration and an extended configuration, and wherein a length of the adjustable cage in the retracted configuration is smaller than the length of the adjustable cage in the extended configuration.

11. The system of claim 1, wherein the adjustable cage has a contracted configuration and an expanded configuration, and wherein an outer dimension of the adjustable cage in the contracted configuration is smaller than the outer dimension of the adjustable cage in the expanded configuration.

12. The system of claim 1, wherein the flexible tubular member comprises a multilayer construction having layers selected from the list consisting of a polymer layer, a braid layer, and a helical coil layer.

13. The system of claim 1, wherein the plurality of flexible elements are disposed through openings in a distal end of the flexible tubular member.

14. The system of claim 13, wherein the openings have axes, each of said axes being oriented at an oblique angle with respect to a longitudinal axis of the flexible tubular member.

* * * * *